US012245954B2

(12) United States Patent
Singh et al.

(10) Patent No.: US 12,245,954 B2
(45) Date of Patent: *Mar. 11, 2025

(54) ROBOTIC SYSTEM FOR ANKLE ARTHROPLASTY

(71) Applicant: MAKO Surgical Corp., Weston, FL (US)

(72) Inventors: Manoj Kumar Singh, Mahwah, NJ (US); Yves Crozet, Ramsey, NJ (US); Daniel Greenberg, Ramsey, NJ (US)

(73) Assignee: MAKO Surgical Corp., Weston, FL (US)

( * ) Notice: Subject to any disclaimer, the term of this patent is extended or adjusted under 35 U.S.C. 154(b) by 53 days.

This patent is subject to a terminal disclaimer.

(21) Appl. No.: 18/197,187

(22) Filed: May 15, 2023

(65) Prior Publication Data

US 2023/0277333 A1 Sep. 7, 2023

Related U.S. Application Data

(63) Continuation of application No. 16/665,487, filed on Oct. 28, 2019, now Pat. No. 11,684,489.

(Continued)

(51) Int. Cl.

*A61F 2/46* (2006.01)
*A61B 17/15* (2006.01)

(Continued)

(52) U.S. Cl.

CPC .......... *A61F 2/4606* (2013.01); *A61B 17/151* (2013.01); *A61B 34/20* (2016.02);

(Continued)

(58) Field of Classification Search

CPC ......... A61B 34/10; A61B 34/20; A61B 34/25; A61F 2/4202; A61F 2/4657

See application file for complete search history.

(56) References Cited

U.S. PATENT DOCUMENTS 7,725,162 B2 5/2010 Malackowski et al.
8,010,180 B2 8/2011 Quaid et al.

(Continued)

FOREIGN PATENT DOCUMENTS

WO 2016039762 A1 3/2016
WO 2018045086 A1 3/2018

OTHER PUBLICATIONS

Wright Medical Group N.V., "Infinity Ankle System Webpage and Videos", https://www.wright.com/footandankleproducts/infinity-total-ankle-system, 2020, 4 pages.

*Primary Examiner* — Anu Ramana

(74) *Attorney, Agent, or Firm* — Howard & Howard Attorneys PLLC

(57) ABSTRACT

Robotic system and methods for robotic arthroplasty are provided. The robotic system includes a machining system and a guidance system. The guidance station tracks movement of one or more of various objects in the operating room, such as a surgical tool, a tibia of a patient, a talus of the patient, or a component of an implant. The guidance system tracks these objects for purposes of displaying their relative positions and orientations to the surgeon and, in some cases, for purposes of controlling movement of the surgical tool of the machining system relative to virtual cutting boundaries or other virtual objects associated with the tibia and talus to facilitate preparation of bone to receive an ankle implant system.

20 Claims, 15 Drawing Sheets

Related U.S. Application Data

(60) Provisional application No. 62/751,957, filed on Oct. 29, 2018.

(51) Int. Cl.
*A61B 34/00* (2016.01)
*A61B 34/20* (2016.01)
*A61B 34/32* (2016.01)

(52) U.S. Cl.
CPC .............. *A61B 34/25* (2016.02); *A61B 34/32* (2016.02); *A61F 2/4657* (2013.01); *A61B 2034/2055* (2016.02); *A61B 2034/2057* (2016.02); *A61B 2034/2059* (2016.02); *A61B 2034/2068* (2016.02); *A61B 2034/252* (2016.02); *A61F 2002/4633* (2013.01)

(56) References Cited

U.S. PATENT DOCUMENTS

| | | | |
|---|---|---|---|
| 8,457,719 B2 | 6/2013 | Moctezuma de la Barrera et al. | |
| 9,008,757 B2 | 4/2015 | Wu | |
| 9,119,655 B2 | 9/2015 | Bowling et al. | |
| 9,566,120 B2 | 2/2017 | Malackowski et al. | |
| 10,485,450 B2 * | 11/2019 | Gupta | A61B 34/20 |
| 2010/0262150 A1 | 10/2010 | Lian | |
| 2017/0258526 A1 | 9/2017 | Lang | |
| 2017/0340450 A1 | 11/2017 | Toro Arbelaez et al. | |
| 2020/0129311 A1 | 4/2020 | Singh et al. | |

* cited by examiner

ROBOTIC SYSTEM FOR ANKLE ARTHROPLASTY

CROSS-REFERENCE TO RELATED APPLICATIONS

This application is a Continuation of U.S. patent application Ser. No. 16/665,487 filed on Oct. 28, 2019, which claims priority to and the benefit of U.S. Provisional Application No. 62/751,957 filed Oct. 29, 2018, the disclosures of which are each incorporated herein by reference.

TECHNICAL FIELD

The present disclosure relates generally to robotic systems and, more particularly, to robotic systems for ankle arthroplasty.

BACKGROUND

Robotic systems used in surgery are well known. One such system comprises a robotic manipulator and a cutting tool for sculpting bone into a desired shape. The cutting tool is coupled to the robotic manipulator to remove material from the bone for purposes of creating space or features to receive an implant. Typically, these systems are used to prepare bones for hip implants and knee implants. As the world population continues to live longer, there is a growing need for arthroplasty. Owing to the relatively greater need for hip arthroplasty and knee arthroplasty, prior art robotic systems focus on preparing bones for hip and knee procedures. There remains a need for robotic systems for ankle arthroplasty to provide higher accuracy and more precision in replacing ankle joints and to form features in bone for receiving ankle implants.

Ankle arthroplasty commonly involves a three component uncemented implant comprising tibial and talar components and an insert disposed between the tibial and talar components. The procedure to install the implant typically includes manually preparing a patient's tibia to receive the tibial component secured by anchoring to the tibia; and preparing a patient's talus to receive the talar component. The surgeon may employ mechanical cutting guides and other aids that assist in performing the necessary cutting. These mechanical guides and aids require mounting to the patient's bone and typically require larger sized openings or multiple openings in the anatomy and penetrations into the bone. To prepare the talus, several dome cuts are made in order for the talar dome component to be seated on top of the talus, forming a cap on the top and around all four sides. The installation of the talar component conceals the resected aspects of the talus, preventing direct inspection of the placement of the talar component on the talus. Thus, there is a desire and a need for improved systems and methods that securely place such implant on the talus, and to provide for inspection and verification of the placement of the implant on the talus.

BRIEF DESCRIPTION OF THE DRAWINGS

Advantages of the present disclosure will be readily appreciated as the same becomes better understood by reference to the following detailed description when considered in connection with the accompanying drawings.

SUMMARY

Figure 1:
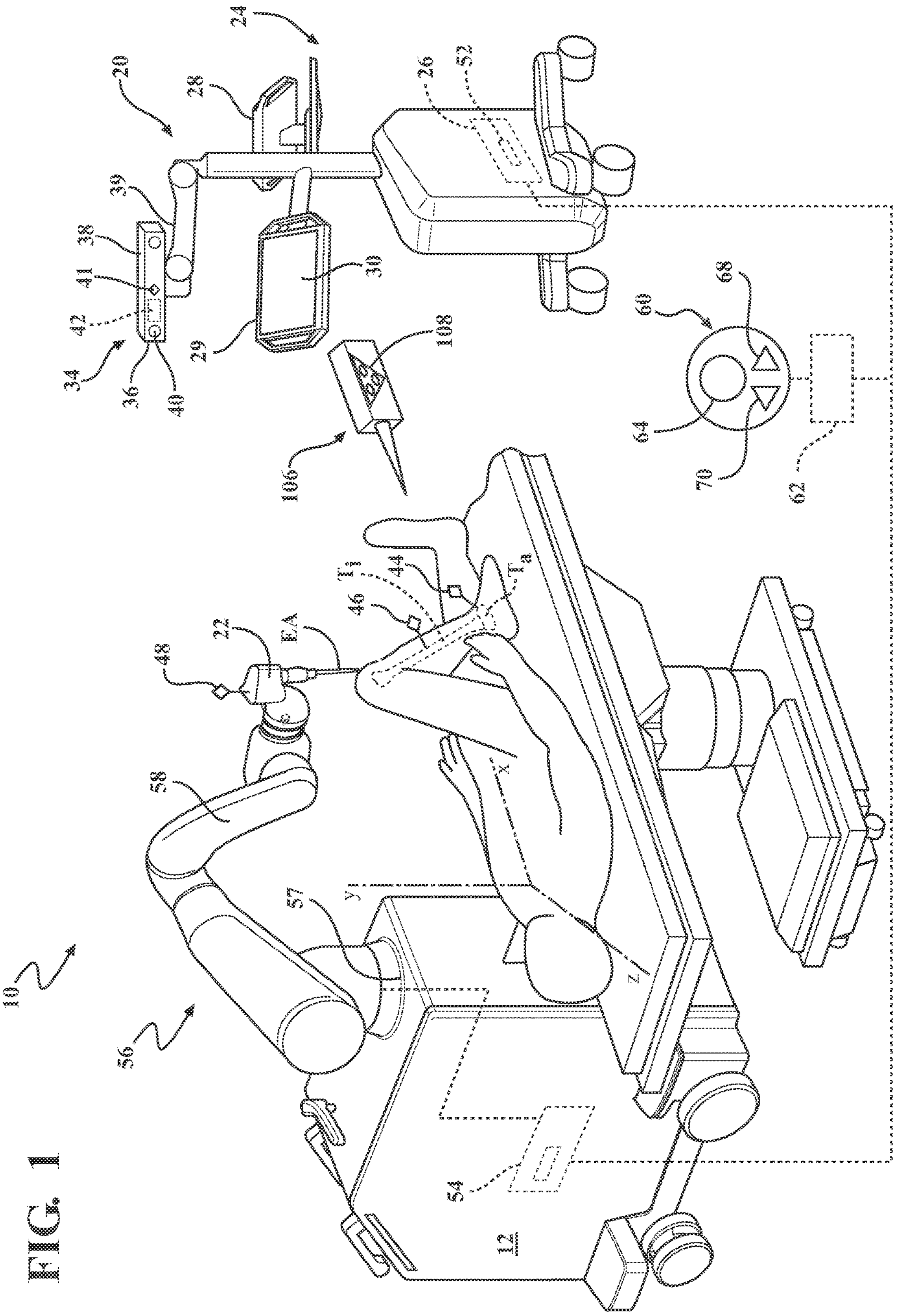
FIG. 1 is a perspective view of a robotic system for ankle arthroplasty.

A method is provided for verifying a talar implant placement on a talus wherein the talar implant has a known geometry. The method includes the action of registering the talus for tracking with a computer surgical system. The method includes placing the talar implant on the talus. The method includes registering the talar implant for tracking with the computer surgical system. The method also includes determining the talar implant placement on the talus.

A robotic surgery system is provided for preparing an ankle joint to receive an ankle joint replacement wherein the ankle joint replacement includes a tibia component, a poly component, and a talar component. The robotic surgery system includes a robotic manipulator. The robotic surgery system includes a cutting tool to be coupled to the robotic manipulator. The robotic surgery system includes a localizer configured to track movement of one or more trackers. The robotic surgery system also includes a controller coupled to the robotic manipulator and the localizer, the controller configured to operate the robotic manipulator to control movement of the cutting tool relative to the ankle joint based on one or more virtual objects associated with the ankle joint replacement. In the robotic surgery system, the one or more virtual objects define a volume of material to be removed from a talus of the ankle joint to form a pyramidal frustum to receive the talar component, wherein the pyramidal frustum defines a complementary contour to an interior concavity of the talar component.

A method is provided for performing robotic surgery with a robotic manipulator and a cutting tool coupled to the robotic manipulator to prepare an ankle joint comprising a tibia and a talus, to receive an ankle joint replacement. The ankle joint replacement has a tibia component, a poly component and a talar component. The method includes tracking movement of the cutting tool. The method includes tracking movement of the talus. The method includes controlling movement of the cutting tool relative to the talus based on one or more virtual objects associated with the ankle joint replacement to form a pyramidal frustum on the talus adapted to receive the talar component, wherein the pyramidal frustum defines a complementary contour to an interior concavity of the talar component.

A computer surgical system is provided for verifying a placement of a talar implant placed on a talus bone, the talus bone and talar implant having a known geometry represented by virtual models in a virtual environment. The system includes a display. The system includes a guidance station to track a movement of virtual models of objects. The guidance station is in electronic communication with the display. The guidance station is configured to store a virtual model of the talar implant in a memory. The guidance station is configured to store a virtual model of the talus bone in the memory. The guidance station is configured to retrieve from the memory data representing a relative positioning of the virtual model of the talar implant to the virtual model of the talus bone. The guidance station is also configured to determine a placement of the virtual model of the talar implant on the virtual model of the talus bone to verify a proper seating or to represent an improper seating of the talar implant on the talus bone.

A method is provided for verifying a placement of a talar implant placed on a talus bone, the talus bone and talar implant having a known geometry represented by virtual models in a virtual environment. The method includes storing a virtual model of the talar implant in a memory of a guidance station. The method includes storing a virtual model of the talus bone in a memory of the guidance station. The method includes retrieving from the memory of the guidance station a relative position of the virtual model of the talar implant to the virtual model of the talus bone. The method includes determining a placement of the virtual model of the talar implant on the virtual model of the talus bone to verify a proper seating or to represent an improper seating of the talar implant on the talus bone.

A non-tangible computer readable storage medium is provided comprising computer readable instructions that when executed cause a computer system to perform the steps of the disclosed methods.

DETAILED DESCRIPTION

Referring to FIG. 1, a computer surgical system is shown as a robotic system 10 for performing surgery on a patient. The version shown in FIG. 1 comprises a material removal system for removing material from a workpiece (e.g., bone), but it should be appreciated that other types of computer surgical systems are also contemplated, such as, for example a computer surgical system that provides machine vision or optical navigation and guidance for manual surgical operations. The robotic system 10 is shown in a surgical setting such as an operating room of a medical facility. In the figure as shown, the robotic system 10 includes a machining station 12 and a guidance station 20.

The guidance station 20 is set up to track movement of various objects in the operating room. Such objects include, for example, a surgical tool 22, a tibia Ti of a patient, and a talus Ta of the patient. The guidance station 20 tracks these objects for purposes of displaying their relative positions and orientations to the surgeon and, in some cases, for purposes of controlling movement (e.g., causing movement, guiding movement, constraining movement, etc.) of the surgical tool 22 relative to virtual cutting boundaries or other virtual objects associated with the tibia Ti and talus Ta.

The guidance station 20 includes a computer cart assembly 24 that houses a navigation controller 26. A navigation interface is in operative communication with the navigation controller 26. The navigation interface includes a first display 28 adapted to be situated outside of a sterile field and a second display 29 adapted to be situated inside the sterile field. The displays 28, 29 are adjustably mounted to the computer cart assembly 24. First and second input devices (not shown) such as a keyboard and mouse can be used to input information into the navigation controller 26 or otherwise select/control certain aspects of the navigation controller 26. Other input devices are contemplated, including a touch screen 30 or voice-activation.

A localizer 34 communicates with the navigation controller 26. In the illustration as shown, the localizer 34 is an optical localizer and includes a camera unit 36. Other types of localizers are also contemplated, including localizers that employ ultrasound, radio frequency (RF) signals, electromagnetic fields, and the like. The camera unit 36 has an outer casing 38 that houses one or more optical position sensors 40. In some alternatives at least two optical sensors 40 are employed, or alternatively three or four optical sensors 40. The optical sensors 40 may be two, two-dimensional charge-coupled devices (CCD). In one example, four, one-dimensional CCDs are employed. It should be appreciated that in other alternatives, multiple, separate camera units 36, each with a separate CCD, or two or more CCDs, could also be arranged around the operating room. The CCDs may be adapted to detect infrared (IR) signals, or may be adapted to sense in the visible spectrum. The localizer 34 may further include one or more additional sensors 41, such as a video camera, or laser range finder.

The camera unit 36 is mounted on an adjustable arm 39 to position the optical sensors 40 with a field of view of the below discussed trackers that, ideally, is free from obstructions. In some alternatives, the camera unit 36 is adjustable in at least one degree of freedom by rotating about a rotational joint. In other alternatives, the camera unit 36 is adjustable about two or more degrees of freedom.

The camera unit 36 includes a camera controller 42 in communication with the optical sensors 40 to receive signals from the optical sensors 40. The camera controller 42 communicates with the navigation controller 26 through either a wired or wireless connection (not shown). One such connection may be an IEEE 1394 interface, which is a serial bus interface standard for high-speed communications and isochronous real-time data transfer. The connection could also use a company specific protocol. In other alternatives, the optical sensors 40 communicate directly with the navigation controller 26.

Position and orientation signals and/or data are transmitted to the navigation controller 26 for purposes of tracking objects. The computer cart assembly 24, display 28, and camera unit 36 may be like those described in U.S. Pat. No.

7,725,162 to Malackowski, et al. issued on May 25, 2010, entitled "Surgery System," hereby incorporated by reference.

The navigation controller 26 can be a personal computer or laptop computer. The navigation controller 26 has the display 28, central processing unit (CPU) and/or other processors, memory (not shown), and storage (not shown). The navigation controller 26 is loaded with software. The software converts the signals received from the camera unit 36 into data representative of the position and orientation of the objects being tracked. Alternatively, the camera controller 42 may further include memory (not shown), and storage (not shown), and may be loaded with software to convert the signals received from the position sensors 40, and/or additional sensors 41, into data representative of the position and orientation of the objects being tracked.

The guidance station 20 is operable with a plurality of tracking devices 44, 46, 48, also referred to herein as trackers. In the illustrated alternative, one tracker 44 is firmly affixed to the talus Ta of the patient and another tracker 46 is firmly affixed to the tibia Ti of the patient. The trackers 44, 46 are firmly affixed to sections of bone. The trackers 44, 46 could be mounted like those shown in U.S. Pat. No. 9,566,120, issued on Feb. 14, 2014, entitled, "Navigation Systems and Methods for Indicating and Reducing Line-of-Sight Errors," the entire disclosure of which is hereby incorporated by reference. The trackers 44, 46 or other trackers could be mounted to other tissue types, parts of the anatomy, tools, implants or other objects in the operating environment.

Various types of trackers could be employed, including rigid trackers or flexible trackers like those shown in U.S. Pat. No. 8,457,719 to Moctezuma de la Barrera et al., entitled "Flexible Tracking Article and Method of Using the Same," filed on Dec. 8, 2010, which is hereby incorporated by reference. For example, the SpineMask® Non-Invasive Tracker sold by Stryker Navigation (an operating division of Stryker Corporation), 4100 East Milham Ave., Kalamazoo, Michigan, could be employed.

A tool tracker 48 is firmly attached to the surgical tool 22. The tool tracker 48 may be integrated into the surgical tool 22 during manufacture or may be separately mounted to the surgical tool 22 in preparation for surgical procedures. In the alternative shown, the surgical tool 22 is attached to a manipulator 56 of the machining station 12. Such an arrangement is shown in U.S. Pat. No. 9,119,655, issued Sep. 1, 2015, entitled, "Surgical Manipulator Capable of Controlling a Surgical Instrument in Multiple Modes," the entire disclosure of which is hereby incorporated by reference.

A separate tracker (not shown) may be attached to or integrated with a base 57 of the manipulator 56 to track movement of the base 57 in some alternatives. In this case, the working end of the surgical tool 22 may be tracked via the base tracker by virtue of additional encoder data being provided by encoders in joints of the manipulator 56, which provide joint position data that can be processed collectively to generate information regarding a location of the working end of the surgical tool 22 relative to the base 57. The working end of the surgical tool 22, which is being tracked by virtue of the tool tracker 48 (or base tracker in some cases), may be an energy applicator EA such as a rotating burr, saw blade, electrical ablation device, special purpose probe, or the like. The energy applicator EA may be a separate component that is releasably connected to a handpiece of the surgical tool 22 or may be integrally formed with the handpiece.

The trackers 44, 46, 48 can be battery powered with an internal battery or may have leads to receive power through the navigation controller 26, which, like the camera unit 36, receives external power. The trackers may be active trackers, generating and emitting radiant energy, such as infrared light, or passive trackers, reflecting radiant energy generated and emitted, for example, by an infrared LED (not shown) of the camera unit 36.

The optical sensors 40 of the localizer 34 receive light signals from the trackers 44, 46, 48. In this alternative, each tracker 44, 46, 48 has at least three tracking elements or markers for transmitting light to the optical sensors 40. The markers, if active, can be, for example, light emitting diodes or LEDs 50 (see FIG. 2) transmitting light, such as infrared light. The optical sensors 40 may have sampling rates of 100 Hz or more, more preferably 300 Hz or more, and most preferably 500 Hz or more. In some alternatives, the optical sensors 40 have sampling rates of 8000 Hz. The sampling rate is the rate at which the optical sensors 40 receive light signals from sequentially fired LEDs (not shown), or is the rate at which information is cyclically read out from the two-dimensional CCD sensor matrix. In some alternatives, the light signals from the LEDs 50 are fired at different rates for each tracker 44, 46, 48.

The LEDs 50 may be connected to a tracker controller (not shown) located in a housing of the associated tracker 44, 46, 48 that transmits/receives data to/from the navigation controller 26. In one alternative, the tracker controllers transmit data on the order of several Megabytes/second through wired connections with the navigation controller 26. In other alternatives, a wireless connection may be used. In these alternatives, the navigation controller 26 has a transceiver (not shown) to receive the data from the tracker controller.

In some alternatives, the trackers 44, 46, 48 also include a gyroscope sensor and accelerometer, inertial sensor, or the like, such as the trackers shown in U.S. Pat. No. 9,008,757, issued on Apr. 14, 2015, entitled, "Navigation System Including Optical and Non-Optical Sensors," the entire disclosure of which is hereby incorporated by reference. The additional sensors may generate signals communicate to one or more of the camera controller, or navigation controller, which may be used in combination with other signals to generate tracking and positioning information.

The navigation controller 26 includes a navigation processor 52. It should be understood that the navigation processor 52 could include one or more processors to control operation of the navigation controller 26. The processors can be any type of microprocessor or multi-processor system. The navigation controller 26 may additionally or alternatively comprise one or more microcontrollers, field programmable gate arrays, systems on a chip, discrete circuitry, and/or other suitable hardware, software, or firmware that is capable of carrying out the functions described herein. The term processor is not intended to limit the scope of any alternative to a single processor.

The camera unit 36 receives optical signals from the LEDs 50 of the trackers 44, 46, 48 and outputs to the processor 52 signals relating to the position of the LEDs 50 of the trackers 44, 46, 48 relative to the localizer 34. Based on the received optical (and non-optical signals in some alternatives), navigation processor 52, or camera controller 42, generates data indicating the relative positions and orientations of the trackers 44, 46, 48 relative to the localizer 34 using triangulation and/or other techniques.

Prior to the start of the surgical procedure, additional data may be loaded into the navigation processor 52. Based on the position and orientation of the trackers 44, 46, 48 and the previously loaded data, the navigation processor 52 determines the position of the working end of the surgical tool 22 (e.g., the centroid of a surgical burr, cutting envelope of a sagittal saw, etc.) and the orientation of the surgical tool 22 relative to the tissue against which the working end is to be applied. In some alternatives, the navigation processor 52 forwards these data to a manipulator controller 54. The manipulator controller 54 can then use the data to control the manipulator 56 as described in U.S. Pat. No. 9,119,655, issued Sep. 1, 2015, entitled, "Surgical Manipulator Capable of Controlling a Surgical Instrument in Multiple Modes," the entire disclosure of which is hereby incorporated by reference.

In one alternative, the surgical tool 22 is controlled to stay within one or more preoperatively defined virtual boundaries set by the surgeon, which defines the material (e.g., tissue) of the tibia Ti and talus Ta to be removed by the surgical tool 22. These boundaries are defined by virtual objects stored in memory in the robotic system 10 (e.g., in the navigation controller 26 and/or the manipulator controller 54). The boundaries may be defined within a virtual model of the tibia Ti and talus Ta and may be represented as a mesh surface, constructive solid geometry (CSG), voxels, or may be represented using other boundary representation techniques. The boundaries may also be defined separately from virtual models of the tibia Ti and talus Ta. For example, the boundaries may be defined within a virtual representation of the surgical environment as a virtual object having a location relative to the other virtual models or objects.

The navigation processor 52 also generates image signals that indicate the relative position of the working end of the surgical tool 22 to the tissue to be removed. These image signals are applied to the displays 28, 29. The displays 28, 29, based on these signals, generate images that allow the surgeon and staff to view the relative position of the working end to the surgical site. The displays, 28, 29, as discussed above, may include a touch screen or other input/output device that allows entry of commands.

In the alternative shown in FIG. 1, the surgical tool 22 forms part of an end effector of the manipulator 56. The manipulator 56 has a plurality of links 58 extending from the base 57, and a plurality of active joints (not numbered) for moving the surgical tool 22 with respect to the base 57. The links 58 may form a serial robotic arm structure as shown, a parallel robotic arm structure (not shown), or other suitable structure.

The manipulator 56 has the ability to operate in one or more of: (1) a free mode in which a user grasps the end effector of the manipulator 56 in order to cause movement of the surgical tool 22 (e.g., directly, through force/torque sensor measurements that cause active driving of the manipulator 56, passively, or otherwise); (2) a haptic mode in which the user grasps the end effector of the manipulator 56 to cause movement as in the free mode, but is restricted in movement by the virtual boundaries defined by the virtual objects stored in the robotic system 10; (3) a semi-autonomous mode in which the surgical tool 22 is moved by the manipulator 56 along a tool path (e.g., the active joints of the manipulator 56 are operated to move the surgical tool 22 without requiring force/torque on the end effector from the user); (4) a service mode in which the manipulator 56 performs preprogrammed automated movements to enable servicing; or (5) other modes to facilitate preparation of the manipulator 56 for use, e.g., for draping, etc. Examples of operation in the haptic mode and the semi-autonomous mode are described in U.S. Pat. No. 8,010,180, issued Aug. 30, 2011, entitled, "Haptic Guidance System and Method" and U.S. Pat. No. 9,119,655, issued Sep. 1, 2015, entitled, "Surgical Manipulator Capable of Controlling a Surgical Instrument in Multiple Modes," the entire disclosures of both of which are hereby incorporated by reference.

During operation in the haptic mode, for certain surgical tasks, the user manually manipulates (e.g., manually moves or manually causes the movement of) the manipulator 56 to manipulate the surgical tool 22 to perform the surgical procedure on the patient, such as drilling, cutting, reaming, implant installation, and the like. As the user manipulates the surgical tool 22, the guidance station 20 tracks the location of the surgical tool 22 and/or the manipulator 56 and provides haptic feedback (e.g., force feedback) to the user to limit the user's ability to manually move (or manually cause movement of) the surgical tool 22 beyond one or more predefined virtual boundaries that are registered (mapped) to the patient's anatomy, which results in highly accurate and repeatable drilling, cutting, reaming, and/or implant placement.

The manipulator controller 54 may have a central processing unit (CPU) and/or other manipulator processors, memory (not shown), and storage (not shown). The manipulator controller 54 is loaded with software as described below. The manipulator processors could include one or more processors to control operation of the manipulator 56. The processors can be any type of microprocessor, multi-processor, and/or multi-core processing system. The manipulator controller 54 may additionally or alternatively comprise one or more microcontrollers, field programmable gate arrays, systems on a chip, discrete circuitry, and/or other suitable hardware, software, or firmware that is capable of carrying out the functions described herein. The term processor is not intended to limit any alternative to a single processor.

In one version, in the haptic mode, the manipulator controller 54 determines the desired location to which the surgical tool 22 should be moved based on forces and torques applied by the user on the surgical tool 22. In this version, most users are physically unable to actually move the manipulator 56 any appreciable amount to reach the desired position, but the manipulator 56 emulates the user's desired positioning by sensing the applied forces and torques and reacting in a way that gives the user the impression that the user is actually moving the surgical tool 22 even though active motors on the joints are performing the movement. For example, based on the determination of the desired location to which the user wishes to move, and information relating to the current location (e.g., pose) of the surgical tool 22, the manipulator controller 54 determines the extent to which each of the plurality of links 58 needs to be moved in order to reposition the surgical tool 22 from the current location to the desired location. The data regarding where the plurality of links 58 are to be positioned is forwarded to joint motor controllers (not shown) (e.g., one for controlling each motor) that control the active joints of the manipulator 56 to move the plurality of links 58 and thereby move the surgical tool 22 from the current location to the desired location.

A user control pendant assembly 60 may be used to interface with the manipulator controller 54 in the semi-autonomous mode and/or to switch between the free mode, haptic mode, semi-autonomous mode, service mode, and/or other modes. The user control pendant assembly 60 includes a processor or pendant controller 62. The pendant controller 62 may have a central processing unit (CPU) and/or other pendant processors, memory (not shown), and storage (not shown). The pendant controller 62 is in communication with the manipulator controller 54. The pendant controller 62 may be disposed within the pendant assembly 60, or else may be disposed within the machining station 12, the guidance station 20 or combinations thereof with various functions of the pendant controller being divided. The pendant controller 62 is also in communication with switches (not shown) associated with user controls such as buttons 64, 68, 70. The pendant processor could include one or more processors to transmit signals resulting from pressing of buttons 64, 68, 70 on the user control pendant assembly 60 to the manipulator controller 54. Once the practitioner is ready to begin autonomous advancement of the surgical tool 22, in the semi-autonomous mode, for example, the practitioner depresses button 64 (and may be required to hold down button 64 to continue autonomous operation). In some versions, based on the depression of buttons 68 and 70, a feed rate (e.g., velocity) of the working end of the surgical tool 22 may be controlled.

Figure 3:
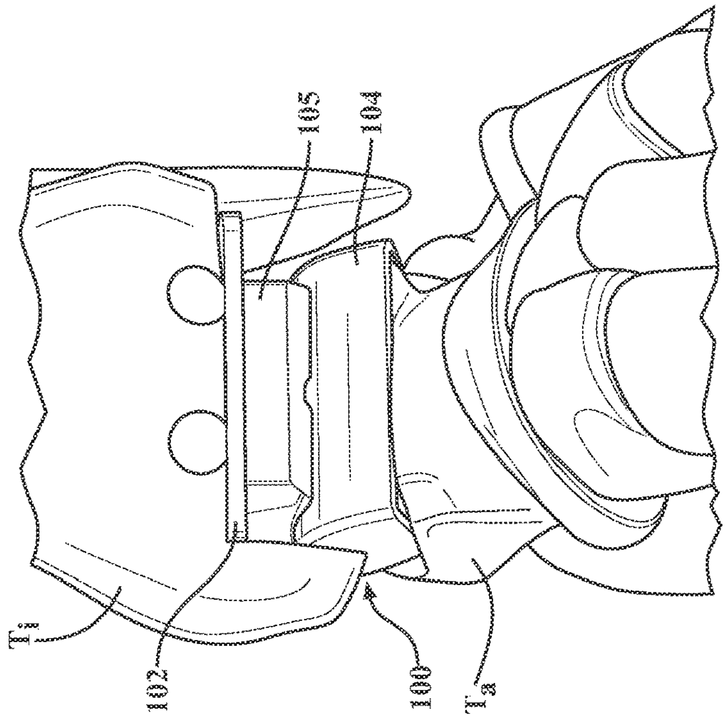
FIG. 3 is an illustration of an ankle implant system replacing the natural ankle joint, including a tibial component, a talar component and an insert.
Figure 2:
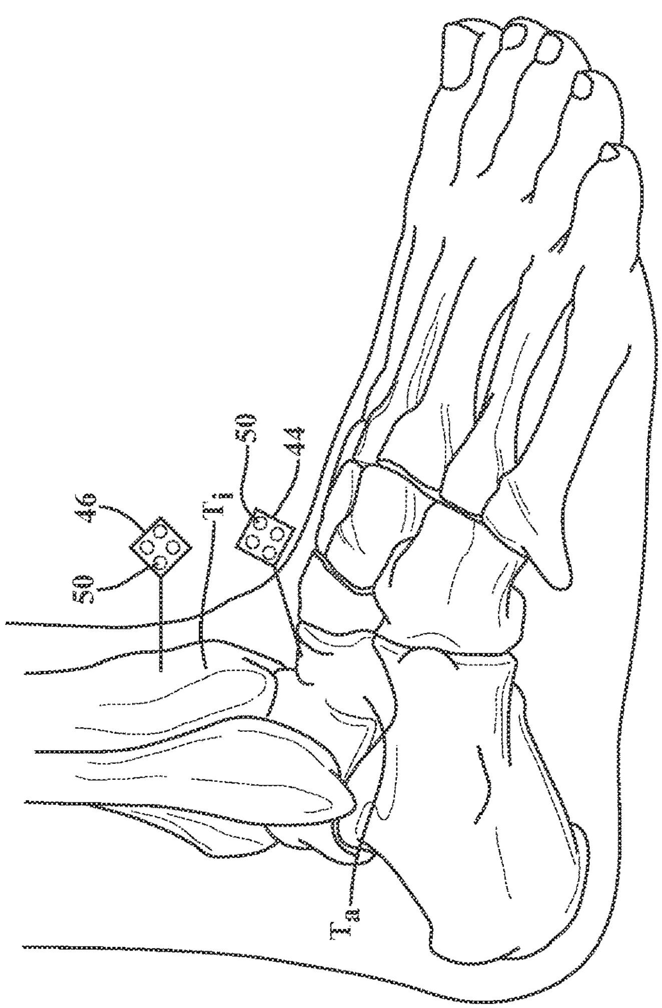
FIG. 2 is an illustration of an ankle joint requiring arthroplasty.

Referring to FIGS. 2 and 3, pre-operative imaging and/or intra-operative imaging may be employed to visualize the patient's anatomy that requires treatment—such as the patient's ankle joint shown in FIG. 2. The surgeon plans where to place an ankle implant system 100, shown in FIG. 3, with respect to the images and/or with respect to one or more 3-D models created from the images, such as 3-D models of the tibia Ti and the talus Ta created from CT scan data, MRI data, or the like. Such models may also be based on generic bone models morphed to resemble patient specific anatomy. Planning includes determining a pose of each implant component of the ankle implant system 100 with respect to the particular bone in which they are being placed, e.g., by identifying the desired pose of the implant component in the images and/or the appropriate 3-D model. This may include creating or positioning a separate 3-D model of the implant components with respect to the 3-D models of the patient's anatomy. Once the plan is set, then the plan is transferred to the robotic system 10 for execution. The 3-D models may comprise mesh surfaces, constructive solid geometries (CSG), voxels, or may be represented using other 3-D modeling techniques.

The robotic system 10 may be employed to prepare the tibia Ti and talus Ta to receive the ankle implant system 100. In this case, the ankle implant system 100 comprises a tibial component 102, a talar component 104, and an insert 105. The insert 105 is also referred to as a mobile bearing. The ankle implant system 100 as illustrated is a non-cemented joint replacement to replace a painful arthritic ankle joint due to osteoarthritis, post-traumatic arthritis, or rheumatoid arthritis. The tibia Ti may be prepared by the robotic system 10 to receive the tibial component 102, and talus Ta may be is prepared by the robotic system 10 to receive the talar component 104.

In the illustrated alternative, the tibial component 102, when viewed from the top, has a trapezoidal shape with rounded corners. On the proximal surface of the tibial component 102, two parallel cylindrical barrels are positioned equidistant from the center of the plate running anterior to posterior for bone fixation. When viewed from the side, the plate is typically about 2.5 mm thick. The distal surface of the plate on which the insert 105 articulates is flat and polished. The tibial component 102 is intended to be press-fit without the use of cement, and should rest on anterior and posterior cortical bone. In one alternative, the tibial component 102 may be formed of a cobalt-chromium-molybdenum alloy (e.g., ASTM F75 standard) with a titanium plasma spray coating (e.g., ASTM F67 standard). The tibial component may be formed using conventional methods as is known in the art.

The tibial component 102 may be sized to correspond to the anatomical space available after tibial resection. For example, the tibial component 102 may be sized between 30 mm×30 mm to 33 mm×45 mm, including multiple alternatives within that range. In select alternatives, the tibial component 102 may be 32 mm×30 mm, 32.5 mm×35 mm, 33 mm×40 mm, or other suitable sizes.

The insert 105, or mobile bearing, has a proximal surface that is flat to interface against the distal surface of the tibial component 102. The distal, or talar, surface of the insert 105 is concave and has a central radial groove running from anterior to posterior. The walls of the insert 105 are straight. A 0.5 mm stainless steel X-ray marker wire is placed 2 mm from the proximal surface within the material of the insert for visibility on X-ray imaging. In one alternative, the insert 105 may be formed of an ultra-high molecular weight polyethylene (e.g., UHMWPe, ASTM F648 standard) and the X-ray marker wire may be formed of stainless steel ASTM F138 standard. The insert 105 may be formed using conventional methods as is known in the art.

The talar component 104 is designed as an anatomical prosthesis to cover the talar dome anterior, posterior, medial and lateral facets. The facets are formed by removing material from the natural growth of the talar dome where the talar component 104 is designed and sized to minimize the amount of bone that must be removed. From the apex of the dome, the walls slope outwards to conform to the normal bone anatomy. Viewed from the side, the proximal surface of the talar component 104 is dome shaped to conform to the talar dome of the natural ankle. A small, raised half-cylindrical ridge runs from the anterior to posterior in the medial-lateral center of the dome. The purpose of the ridge is to constrain the medial/lateral motion of the insert 105. Centrally located on the distal surface of the domed talar component 104, a keel 107 extends within the concavity of talar component 104. The keel 107 is illustrated in more detail in FIG. 11. The keel 107 penetrates into a corresponding keel pocket 135 formed in the talus Ta (see FIG. 10). In one example alternative, the talar component 104 may be formed of a cobalt-chromium-molybdenum alloy (e.g., ASTM F75 standard) with a titanium plasma spray coating (e.g., ASTM F67 standard). The talar component 104 may be formed using conventional methods as is known in the art.

Virtual boundaries, pre-defined tool paths, and/or other autonomous movement instructions, that correspond to the desired placement of the tibial component 102 and the talar component 104 are created to control movement of the manipulator 56 so that the working end of the surgical tool 22 (e.g., burr, drill, saw) is controlled in a manner that ultimately places the components 102, 104 according to the user's plan. This may comprise ensuring during the surgical procedure that the surgical tool 22 (or cutting accessory attached to it) stays within a pre-defined cutting volume delineating the bounds of the material to be removed to receive the implant. This may also comprise, for example, ensuring during the surgical procedure that a trajectory of the surgical tool 22 is aligned with a desired pose of barrel holes. This may further comprise ensuring that a plane of the surgical tool 22 (e.g., for a sagittal saw) is aligned with a desired pose of a planar resection.

The robotic system 10 and/or the user may pre-operatively plan the desired cutting volume, trajectories, planar cuts, etc. For example, the desired cutting volumes may simply correspond to the geometry of the implants being used. Furthermore, these cutting volumes may be virtually located and registered to the anatomy by virtue of the user planning the location of the implants relative to the 3-D models of the tibia Ti and talus Ta and registering the 3-D models of the implants, along with the 3-D models of the tibia Ti and the talus Ta to the actual tibia Ti and the talus Ta during the procedure.

The robotic system 10 and/or the user may also intra-operatively plan the desired cutting volume, trajectories, planar cuts, etc. or may intra-operatively adjust the cutting volumes, trajectories, planar cuts, etc. that were defined pre-operatively. For example, in the free mode, the user could position a drill or burr at a desired entry point relative to the anatomy of interest, e.g., the talus Ta, and orient the drill or burr until the display 28, 29 shows that the trajectory of a rotational axis of the drill or burr is in a desired orientation. Once the user is satisfied with the trajectory, the user provides input to the robotic system 10 to set this trajectory as the desired trajectory to be maintained during the procedure. The input could be provided via input devices such as the mouse, keyboard, touchscreen, push button, foot pedal, pendant control, etc. coupled to the navigation controller 26 or the manipulator controller 54. This same procedure can be followed for the user to set a desired planar cut, etc. 3-D models of the cutting volumes, desired trajectory, desired planar cuts, etc. are stored in memory of the computer surgical system for retrieval during the procedure.

Figure 4:
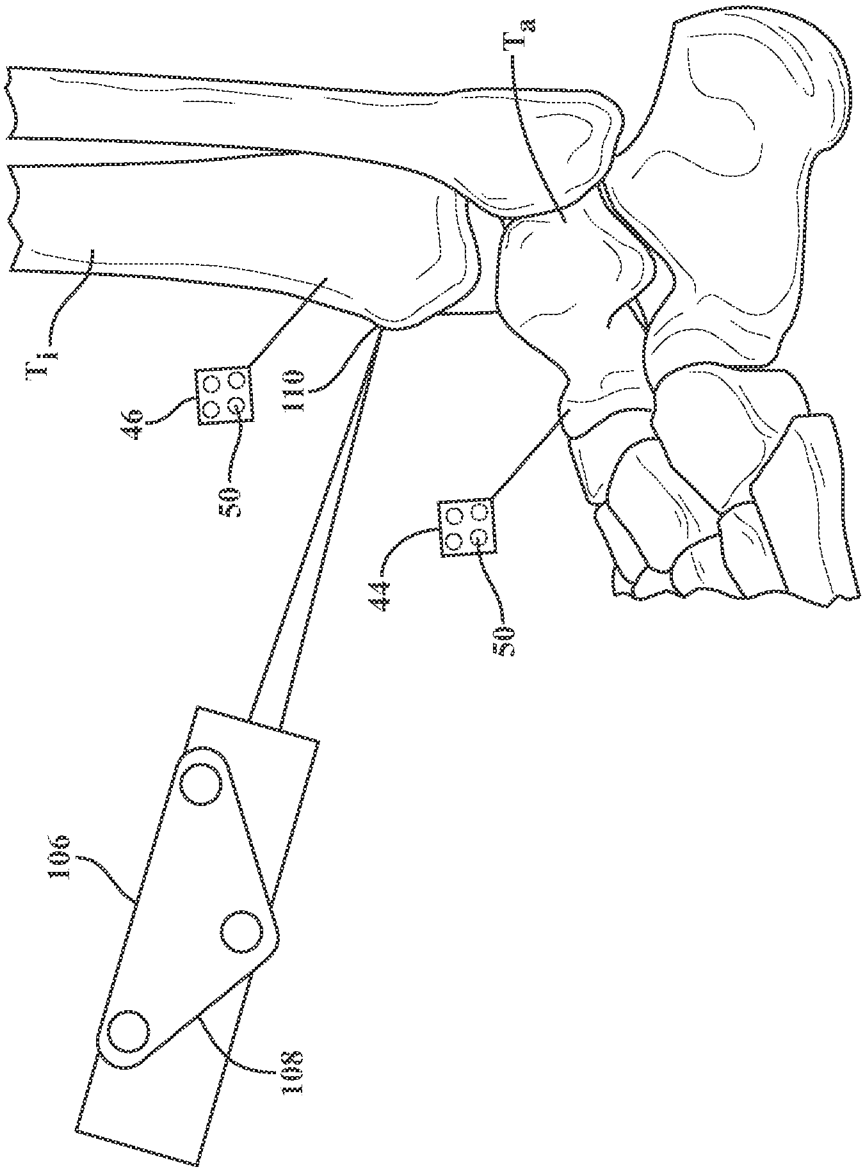
FIG. 4 is an illustration of a navigation pointer being used to locate landmarks on a tibia.

One or more boundaries used by the robotic system 10 could be defined by a navigation pointer 106 by touching anatomy of interest with the navigation pointer 106 and capturing associated points on the anatomy with the guidance station 20. For example, the navigation pointer 106 (FIGS. 1 and 4) could be used to outline the boundary. Additionally, or alternatively, the navigation pointer 106 could be used to delineate soft tissue or other sensitive anatomical structures to be avoided by the surgical tool 22. These points, for example, could be loaded into the robotic system 10 to adjust the tool path to be followed in the semi-autonomous mode so that the surgical tool 22 avoids these areas. Other methods could be used to delineate and/or define anatomy of interest, e.g., as being anatomy to be removed, anatomy to be avoided, etc.

A line virtual/haptic object 161, 163 (see FIG. 16) may be created and stored in the robotic system 10 to constrain movement of the surgical tool 22 to stay along a desired rectilinear trajectory. The line haptic object may have a starting point and a target point, which defines a desired depth of the drill. A planar virtual/haptic object 112, 114 (see FIG. 5) may be created for constraining movement of the surgical tool 22 to stay along a desired plane. Other haptic object shapes, sizes, etc. are also contemplated, including those that define material to be removed to receive the components 102, 104. It should also be appreciated that other forms of virtual objects, other than haptic objects, could be employed to establish boundaries for the surgical tool 22, wherein such boundaries may be represented on one or more of the displays 28, 29 to show the user when the working end of the surgical tool 22 is approaching, reaching, and/or exceeding such boundaries.

Referring to FIGS. 4 through 10 and 16-17, the ankle joint is shown at several stages of preparation for receiving the implant system 100. The description that follows relates to the steps for preparing of the ankle joint to receive the implant system 100, but it should be appreciated that, during a surgical procedure, either of the tibia Ti and the talus Ta may be prepared first to receive its associated implant component, or some combination of alternating preparation steps could be employed. In prior manually performed procedures, the tibia would be prepared first, and the talar cuts would be located in relation to the tibial resections due to the mechanical configurations of the available cut guides. Performing a robotically assisted procedure allows a greater flexibility in selecting and activating the virtual or haptic boundaries or objects guiding the manipulator 56 to prepare the tibia Ti or the talus Ta in the user's preferred sequence.

Figure 5:
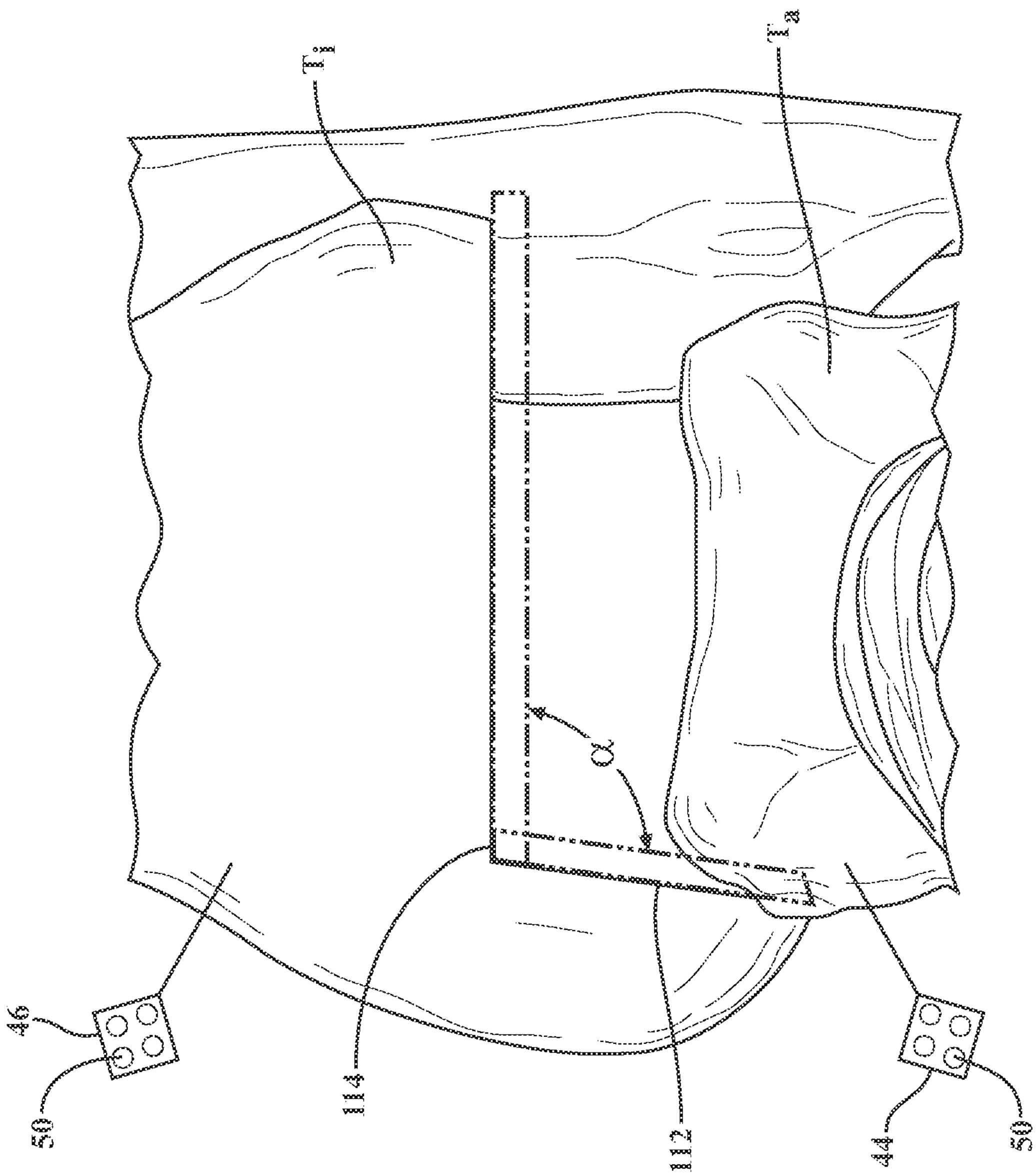
FIG. 5 is a front view of a resected tibia in preparation to receive the tibial component.

As shown in FIG. 5, the tibia Ti is prepared by first defining a resection plane 112 along which the inner edge of the medial malleolus is resected. Thereafter, a transverse distal tibial cut is made along a second resection plane 114. These resections are planar in some alternatives, but may comprise a more complex surface topography in other alternatives. For example, the resection could provide a contoured surface, an undulating surface of ridges, or the like.

One of several options may be employed to determine the location of the resection of the tibia, and by extension the location of the planar virtual/haptic objects 112, 114. In one case, a surgeon may prefer to preoperatively plan the preferred second resection plane 114 orientation to be perpendicular to the tibial diaphysis in both the coronal and sagittal planes; and the preferred first resection plane 112 to be at an angle $\alpha$ relative to the second resection plane 114. In one alternative, the angle $\alpha$ is about 95°. In this case, referring to FIG. 4, the surgeon may establish a virtual resection plane for the resection by using the navigation pointer 106, which comprises its own tracker 108 for purposes of determining a location of its tip 110. The navigation pointer 106 is used in registering pre-operative images or models to actual anatomy being treated during a surgical procedure. Here, the navigation pointer 106 may be used to register a pre-operative 3-D model (e.g., one generated from CT scan data, MRI data, or the like) of the tibia Ti and the talus Ta to the actual tibia Ti and talus Ta and also to define the first and second resection planes 112, 114 of the tibia Ti. Once registered, the trackers 44 and 46 allow the guidance station 20 to track any movement of the tibia Ti or talus Ta and coordinate that movement with the placement of the resection planes 112, 114 for guiding movement of the cutting tool 22 by the manipulator 56. FIG. 5 illustrates the ankle joint, including the virtual objects of the first and second resection planes 112, 114, and the space created by the removal of the material defined by the resection planes.

In order to define the resection of the tibia Ti, the user touches the tip 110 of the navigation pointer 106 to at least three locations along the surface of the tibia Ti, and the navigation controller 26 determines positions of these plurality of landmarks in a coordinate system registered to the tibia Ti (one or more coordinate systems may be employed). Once the positions of the landmarks are determined, the virtual resection planes can be defined relative to the model of the tibia Ti according to the plan. The location of the virtual resection plane defines a location of the planar haptic objects 112, 114 shown in FIG. 5.

Other methods of establishing the resection locations includes placing the resection plane at a predetermined angle (e.g., 90 degrees or other angle) with respect to a longitudinal axis LA of the tibia Ti (e.g. relative to an intramedullary axis of the intramedullary canal) defined in the coordinate system. Yet another method of establishing the plane comprises selecting one or more landmarks on the tibia Ti, and defining the resection based on the one or more landmarks, either alone, or in conjunction with the intramedullary axis of the intramedullary canal and/or in conjunction with an extramedullary axis or axis based on an outer shape of the tibia Ti. A similar registration of the talus Ta, and establishment of the cutting boundaries for preparing the talus Ta is performed for each planned resection of the tibia Ti and talus Ta.

Figure 6:
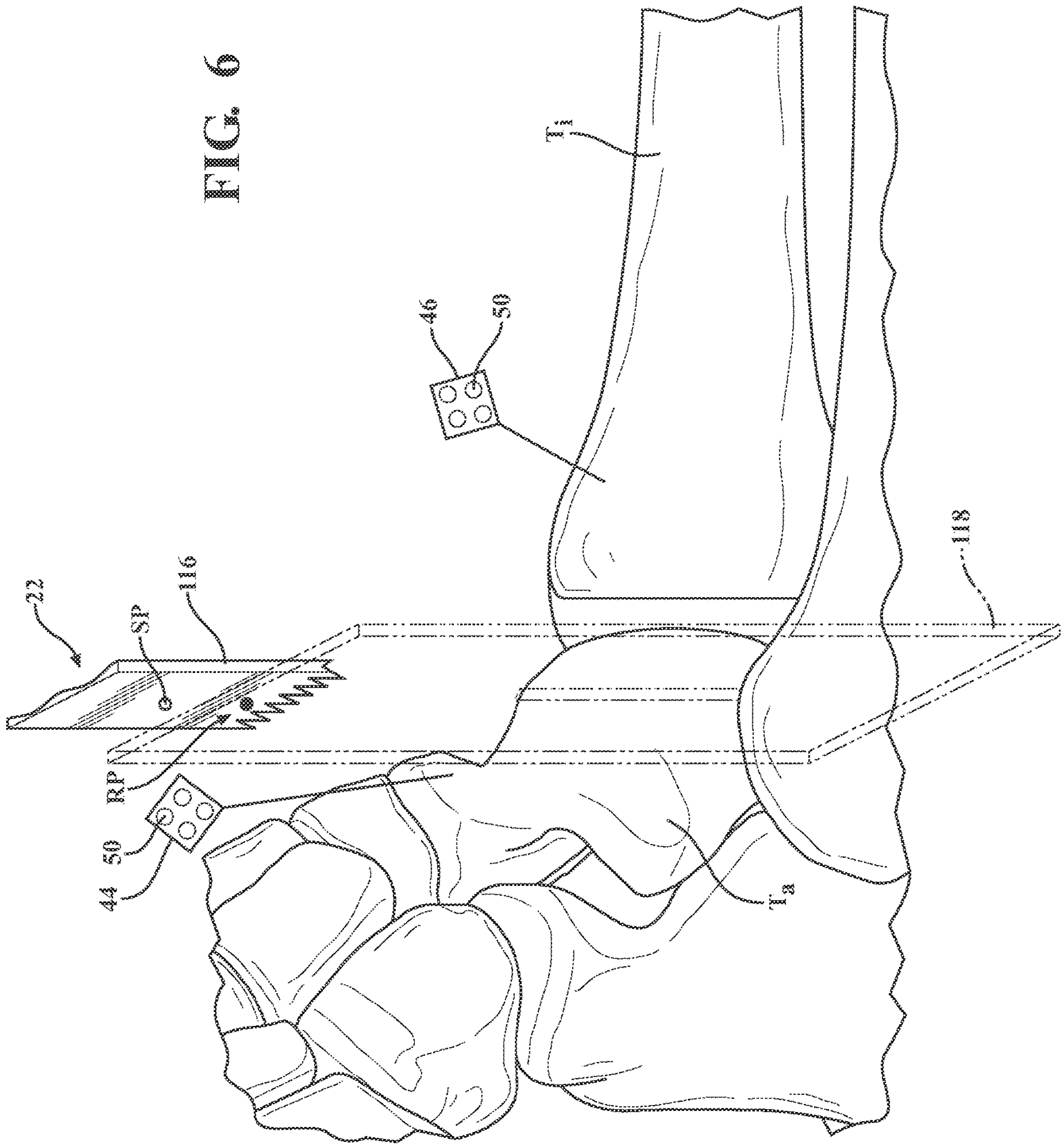
FIG. 6 is an illustration of a virtual object defining a resection plane of the talar dome.

Once the resection location has been determined, the robotic system 10 creates the virtual object required to guide operation of the manipulator 56 and the surgical tool 22 and stores the virtual object in memory. As shown in FIG. 6, the surgical tool 22 comprises a sagittal saw blade 116. The virtual object, in this case the planar haptic object 118, is employed to constrain movement of the saw blade 112 so that the resection is made according to the surgeon's plan. This may include operating the manipulator 56 in the haptic mode and/or semi-autonomous mode to perform the resection. In the haptic mode, the user manually manipulates the surgical tool 22 while the manipulator 56 keeps the saw blade 116 confined within the planar haptic object 118 via haptic feedback to the user or otherwise constraining the movement of the manipulator. In FIG. 6, the planar haptic object 118 is the resection plane for the talar dome.

Visual feedback can additionally be provided on the displays 28, 29, which depict a representation of the saw blade 116 and a representation of the tibia Ti or talus Ta and updates in substantially real-time such representations so that the user and/or others can visualize movement of the saw blade 116 relative to the tibia Ti or talus Ta during resection. The user operates the saw blade 116 to finish the resection and ready the anatomy for further preparation to receive the implant components 102, 104. In some versions, the tibia Ti is manually resected using a conventional sagittal saw, and aided by mechanical cutting guides as is conventional in the art. The conventional sagittal saw, the mechanical cutting guides, and/or the tibia Ti, may be outfitted with navigation trackers so that the user can visualize on the display 28, 29 the relative locations of the tools, the anatomy and the desired resection plane during the operation as a further guide or confirmation to achieve the desired resection while manually resecting the tibia Ti.

In some alternatives, before sawing commences, the robotic system 10 autonomously aligns the saw blade 116 with the desired resection plane. Such autonomous positioning may be initiated by the user pulling a trigger (not shown) on the surgical tool 22, or otherwise providing input to the robotic system 10 to start the autonomous movement. In some cases, a reference point RP of the surgical tool 22 is first brought to within a predefined distance of a starting point SP of the planar haptic object 118 (such as within a predefined starting sphere or starting box). Once the reference point RP is within the predefined distance of the starting point SP, then pulling the trigger (or alternatively pressing a foot pedal or actuating some other input) causes the manipulator 56 to autonomously align and position the saw blade 116 on the desired plane. Once the saw blade 116 is in the desired pose, the robotic system 10 may effectively hold the surgical tool 22 on the desired plane (i.e., within the planar haptic object) by tracking movement of the patient's tracked anatomy, e.g., the tibia Ti, or talus Ta, and autonomously adjusting the manipulator 56 as needed to keep the saw blade 116 on the desired trajectory/plane.

While the robotic system 10 holds the saw blade 116 on the desired plane, the user may then manually manipulate the surgical tool 22 to move (or cause movement of) the saw blade 116 within the planar haptic objects 112, 114, or 118 to resect the bone. In some cases, such as in the haptic mode, the robotic system 10 constrains the user's movement of the surgical tool 22 to stay in the planar haptic object by providing haptic feedback to the user should the user attempt to move the surgical tool 22 in a manner that deviates from the planar haptic objects and the desired plane. If the user desires to return the manipulator 56 to a free mode, for unconstrained movement of the surgical tool 22, the user can then pull the surgical tool 22 back along the planar haptic object 112, 114, or 118, away from the patient, until an exit point of the planar haptic object is reached.

Referring now to FIGS. 7 through 10, the ankle is shown from a side view in plantar flexion with the material of the tibia Ti and the talus Ta removed along the planar haptic objects 112, 114, and 118. Extending the foot in this way exposes the talus to allow the anterior, posterior, lateral and medial facets 128, 130, 132, 134 to be resected on the talus to form a pyramidal frustum where the talar component 104 is supported.

For each facet of the talus to be resected, a corresponding planar virtual/haptic object 120, 122, 124, 126, along the resection plane is created in the guidance station. As described above, the robotic system 10 may autonomously align the saw blade 116 with the desired resection plane. Such autonomous positioning may be initiated by the user pulling a trigger (not shown) on the surgical tool 22, or otherwise providing input to the robotic system 10 to start the autonomous movement. In some cases, a reference point RP of the surgical tool 22 is first brought to within a predefined distance of a starting point SP of the planar haptic object. Once the reference point RP is within the predefined distance of the starting point SP, then the user causes the manipulator 56 to autonomously align and position the saw blade 116 on the desired plane. Once the saw blade 116 is in the desired pose, the robotic system 10 may effectively hold the surgical tool 22 on the desired plane (i.e., within the planar haptic object) by tracking movement of the patient's tracked anatomy, e.g., the tibia Ti, or talus Ta, and autonomously adjusting the manipulator 56 as needed to keep the saw blade 116 on the desired trajectory/plane.

Figure 7:
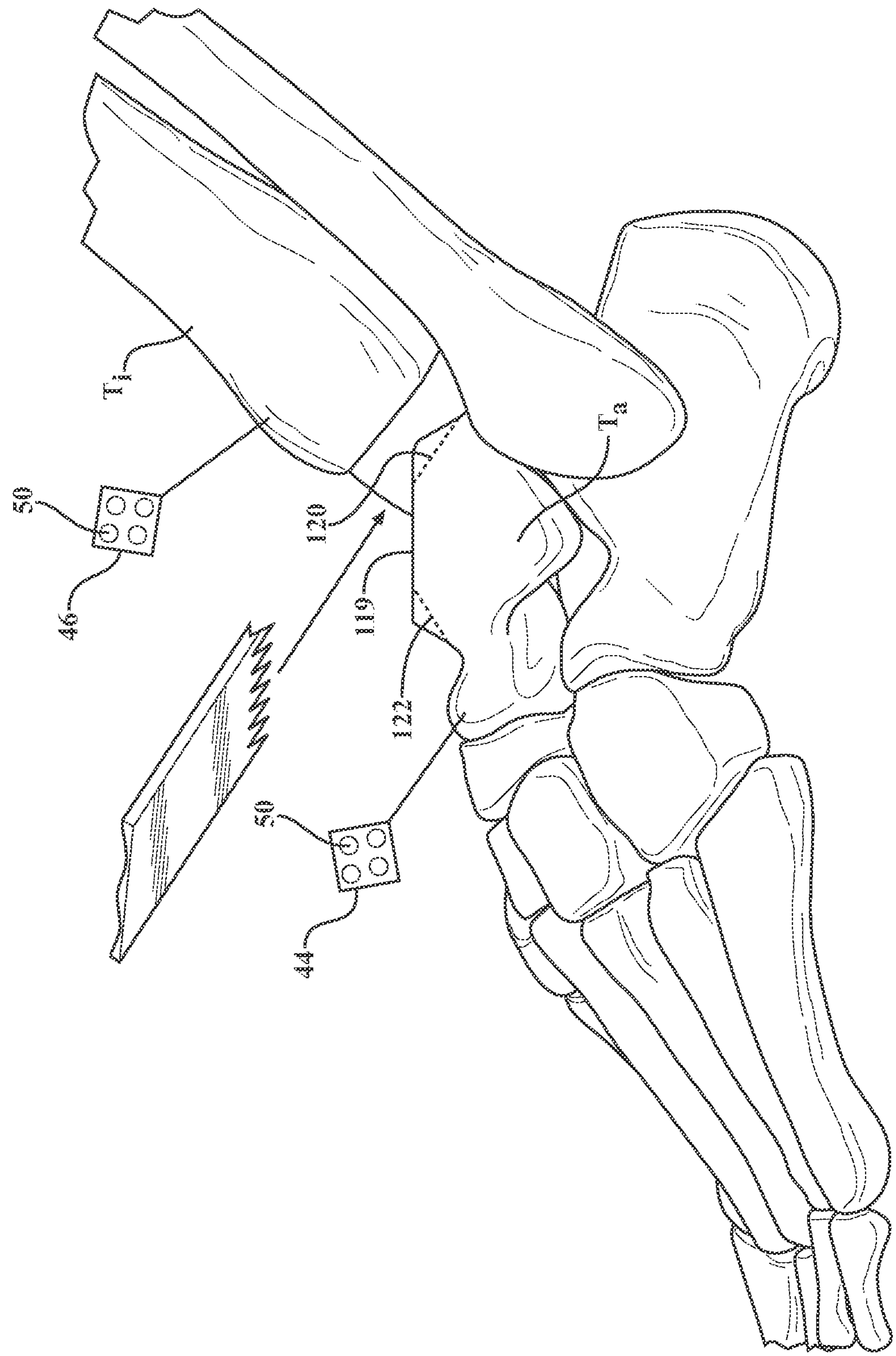
FIG. 7 is a side view of a talus with a first resection and virtual objects defining anterior and posterior resection planes.
Figure 8:
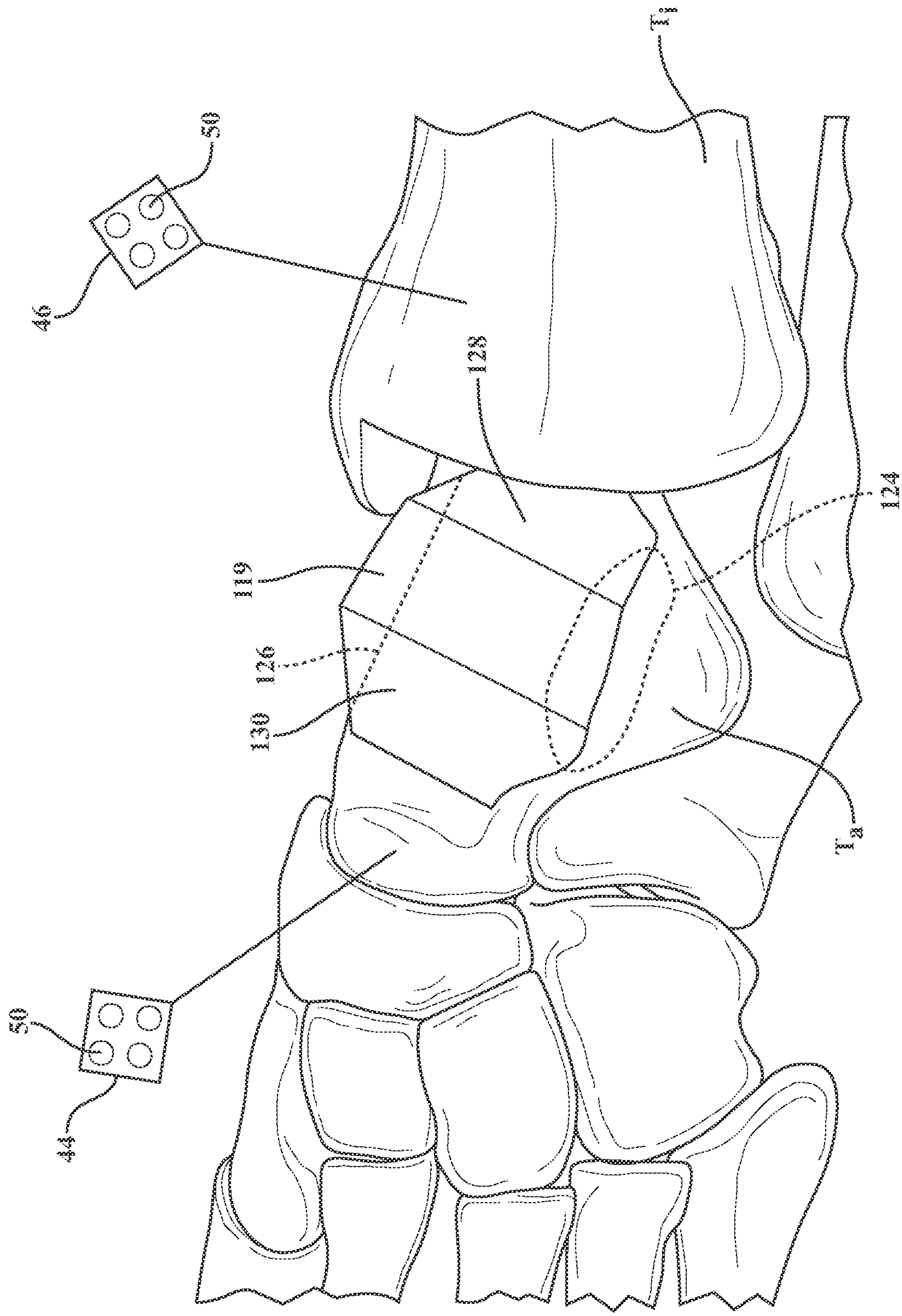
FIG. 8 is a top view of the talus of FIG. 7, further resected, in plantar flexion and showing virtual objects defining medial and lateral resection planes.

FIG. 7 illustrates from the side view the relative positioning of the posterior and anterior haptic planes 120, 122 arranged on the front and back of the talus adjacent to the top, or proximal, facet 119. The user removes the material of the talus by manually moving or causing the robotic system 10 to autonomously move the saw blade 116 within the haptic planes 120, 122. FIG. 8 illustrates from an oblique perspective view the top, posterior and anterior facets 119, 128, 130 of the resected talus Ta. Following formation of the anterior and posterior talar facets 128, 130, the subsequent operations form the medial and lateral facets 132, 134. Similarly, planar virtual/haptic objects 124 and 126 define the resection planes for the medial and lateral facets 132, 134, as shown in FIG. 8.

Figure 9:
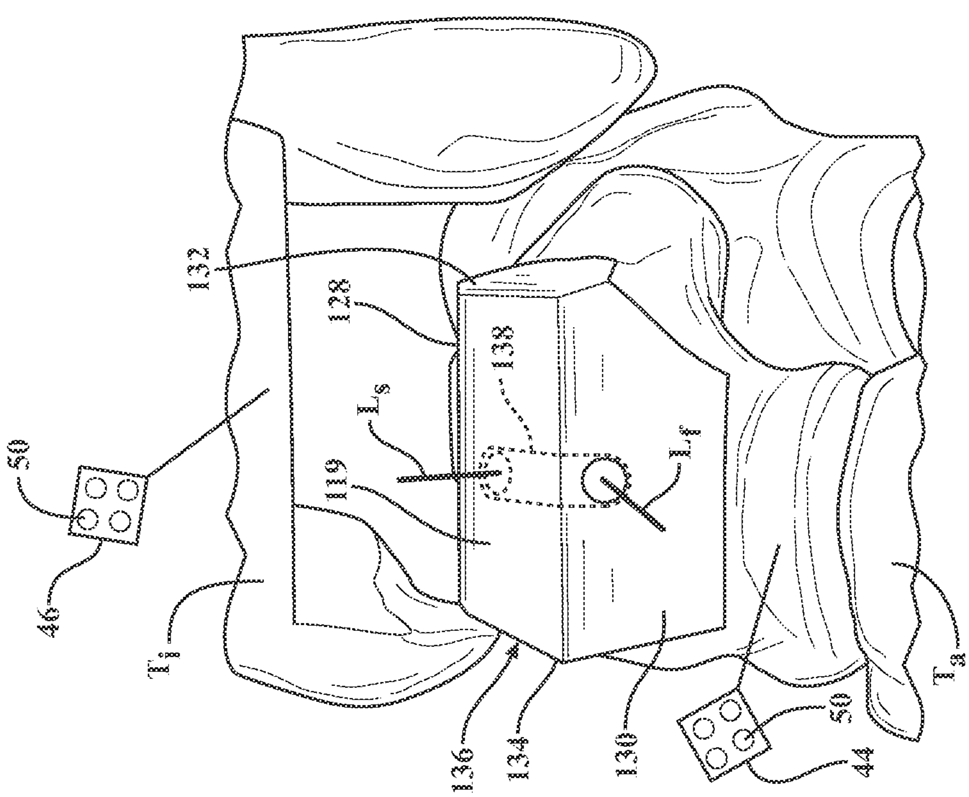
FIG. 9 is a perspective view of the talus of FIG. 8 resected to form a pyramidal frustum.

The faceted pyramidal frustum 136 is illustrated in FIG. 9. To accommodate the keel 107 of the talar component 104, a keel pocket 135 is formed in the talus Ta. In place of the sagittal saw blade 116, a burr, drill, mill, or other energy applicator EA may be coupled to the surgical tool 22 for forming the keel pocket 135. A further step to designate this energy applicator EA placement may be performed to ensure that the guidance station 20 is tracking the cutting aspect of the energy applicator EA based on the location of the tracker 48 coupled to the tool 22. In some alternatives, the energy applicator may include an identifier, such as an RFID tag or other machine readable label, to identify the geometry of a virtual object representing the energy applicator EA. A virtual/haptic volume 138 defines a boundary to constrain the movement of the surgical tool 22 and prevent excessive removal of material from the talus during formation of the keel pocket 135.

Figure 10:
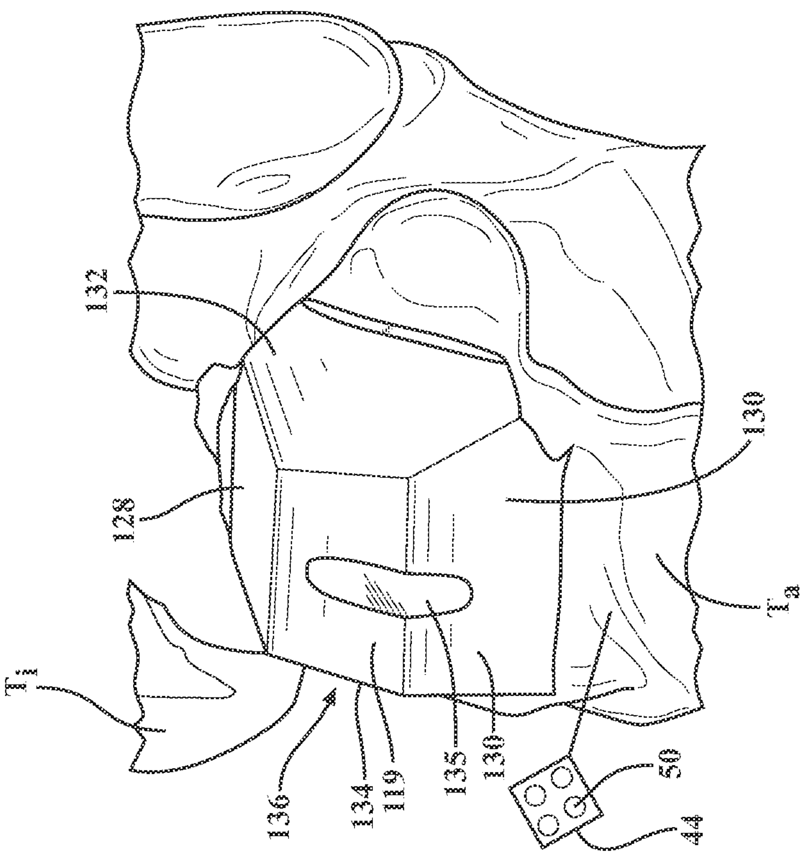
FIG. 10 is a perspective view of the resected talus from another perspective, further including a talar keel pocket.

A linear virtual/haptic object Ls extends linearly from a starting point for forming the keel pocket 135. A user may manually align an axis extending along a burr or drill tool with the linear haptic object Ls. Alternatively, the robotic system 10 may autonomously align the longitudinal axis of the burr or drill with the linear haptic object Ls. Once the axis of the tool is aligned with the linear haptic object, the burr, mill, or drill can be advanced, linearly, into the talus until it reaches the desired depth of the keel pocket 135. The tool is then moved so that the longitudinal axis of the burr, mill or drill reaches the linear haptic object Lf representing the final position of the tool having removed the material necessary to form the keel pocket 135. The tool can be retracted along the linear haptic object Lf to remove it from talus. In one alternative, the tool is moved directly between the starting linear haptic object Ls and final linear haptic object Lf with a compound translation and rotation in a single step. In other alternatives, the tool may be moved through multiple passes, either successively drilling into the talus at multiple positions between the starting and final linear haptic objects Ls, Lf, or translating within the bone at multiple depths between the starting and final linear haptic objects Ls, Lf. In other alternatives, combinations of drilling into and translating the tool through the talus may be employed depending on the tool selected, and the ultimate size and shape of the keel pocket 135 desired. The resulting keel pocket 135 is illustrated in FIG. 10.

Figure 12:
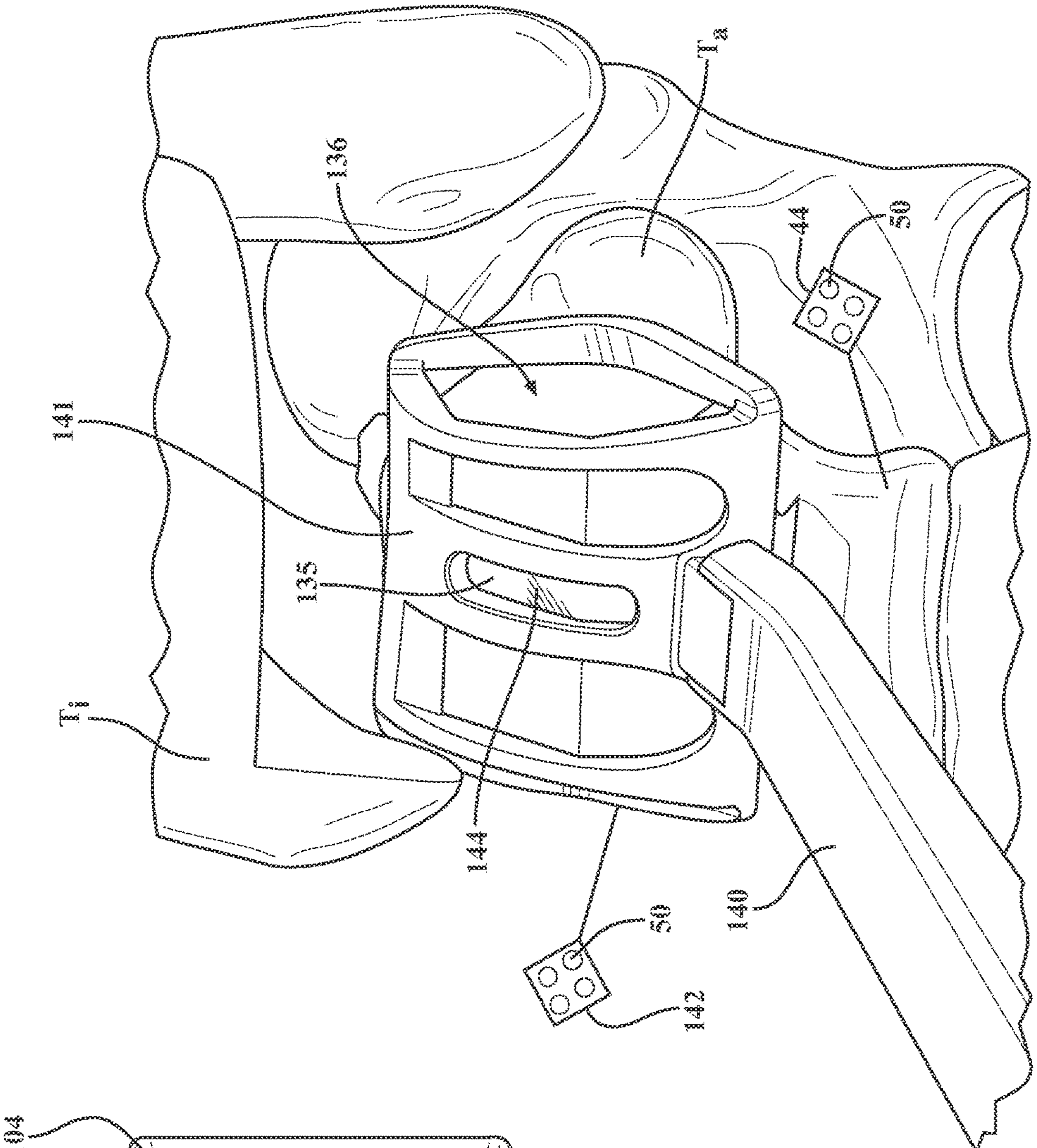
FIG. 12 is a perspective view of a probe of the robotic system in contact with the talar component placed on the pyramidal frustum.
Figure 13:
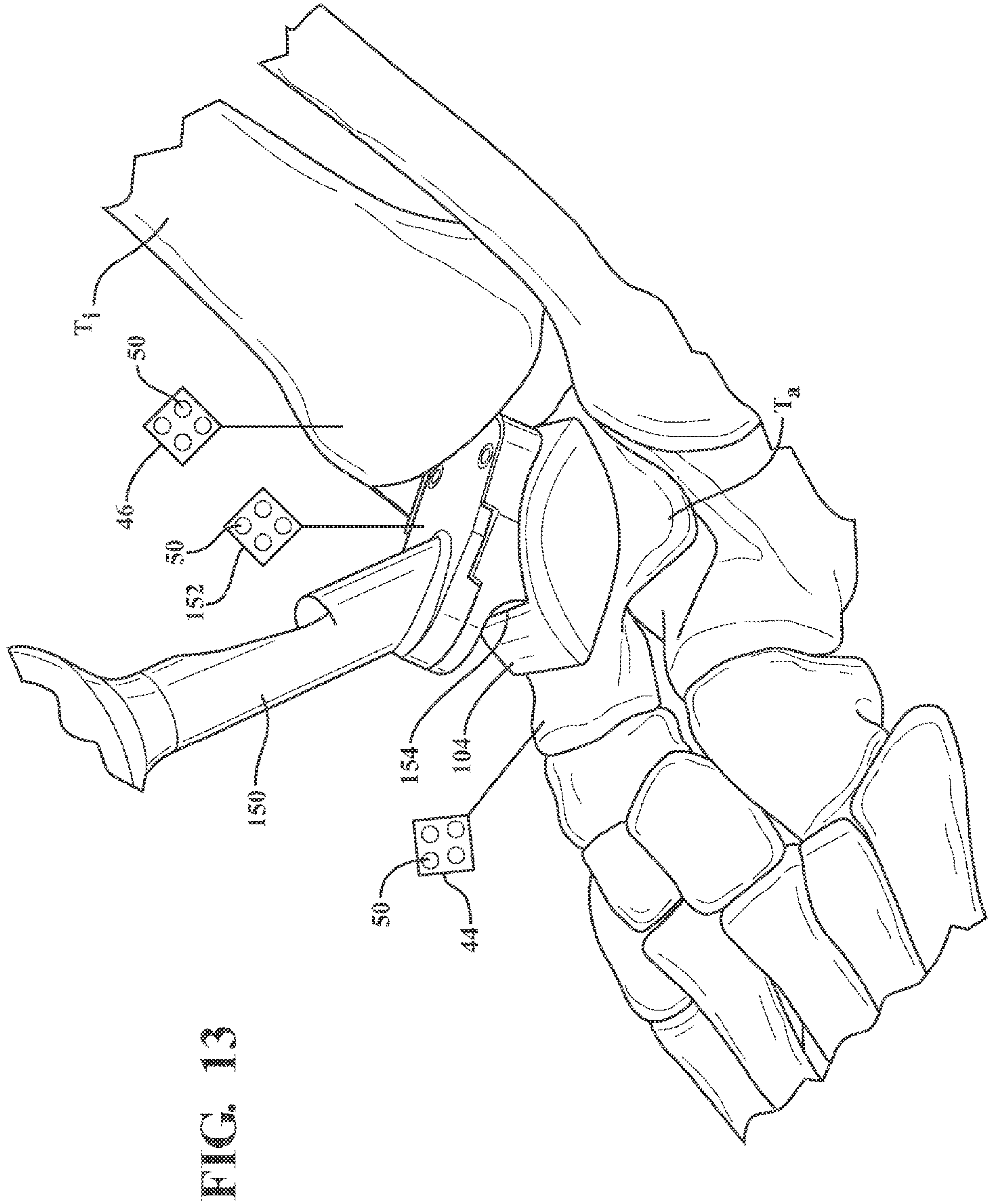
FIG. 13 is an illustration of a tool of the robotic system for installing the talar component.

Installing the implant system 100 includes placing the dome-shaped talar component 104 over the pyramidal frustum 136 created by the resected facets 119, 128, 130, 132, 134 of the talus Ta with the keel 107 penetrating into the keel pocket 135. It is important to the proper function of the ankle implant system 100 for the talar component 104 to be fully seated on the talus Ta and properly positioned according to the surgical plan. The engagement of the talar component 104 to the talus Ta occurs within a concavity of the talar component 104, hidden from the user's view and unavailable for direct inspection. Using the robotic system 10 to resect the tracked tibia Ti and talus Ta allows one way confirm that the resection planes are properly positioned on the anatomy. FIGS. 12 and 13 illustrate additional alternatives for checking the accuracy of the talar resection to the surgical plan. These alternatives may be employed even when the resection is performed manually.

Figure 11:
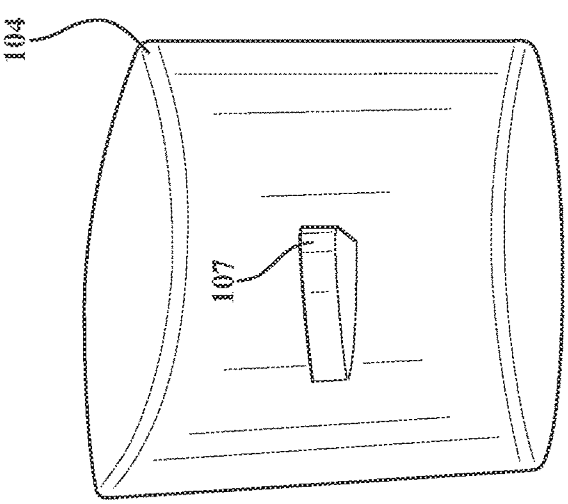
FIG. 11 is a bottom view of the talar component of the ankle implant.

FIG. 12 illustrates a frustum probe 140 placed over the pyramidal frustum 136. The frustum probe 140 includes at its end, a shell structure 141 reproducing the underside geometry of the interior of the talar component 104. The frustum probe 140 may further include a keel extension similar to that of the talar implant 104 (as shown in FIG. 11), or may include a window 144 over the keel pocket 135 to allow the user to visually inspect or access the keel pocket 135.

The frustum probe 140 may be coupled to the manipulator 56, or may include a tracker 142 with a plurality of markers 50 visible to the guidance station 20, or both. The frustum probe 140, through the shell structure 141 and any extension allowing it to be coupled to the surgical tool 22, may have a known geometry, registered to the tracker 142, such that the guidance system 20 can determine the precise geometry of the pyramidal frustum 136 on the talus Ta, where the talus Ta is tracked with the tracker 44. In an alternative example, the frustum probe 140 may be removably coupled to the surgical tool 22, such that the location of the frustum probe 140 can be determined in locating the surgical tool 22 by the tracker 48 coupled to the surgical tool 22 or via a base tracker in combination with joint encoder data integrated within the manipulator 56. In this way, the frustum probe 140 can be used to verify the proper shaping and placement of the pyramidal frustum 136 on the talus Ta where the talus Ta is tracked with tracker 44. The guidance station 20 may be further configured to display guidance to the user on the first and/or second display 28, 29 if it is determined that the shape or placement deviates from the surgical plan based on the relative position of the frustum probe 140 to the talus Ta according to the surgical plan.

In a further alternative, the frustum probe 140 may be one of a set of frustum probes that reproduce not only the underside geometry of the talar component 104, but also the bearing surface on the top of the talar component 104. This alternative may include multiple frustum probes of multiple sizes as a set of trial components to allow the user to evaluate the placement, sizing, and interaction of a talar component of a particular size in the specific application environment of the patient's anatomy. Additionally, in this alternative, each one of the set of frustum probes may include a unique marker pattern on tracker 142 to identify the specific size of the particular probe to the navigation controller 26.

FIG. 13 illustrates a further alternative showing an implant probe 150. Whereas the frustum probe 140 was placed over the talus Ta prior to placing the talar component 104, the implant probe 150 is placed on the talar component 104 after it is seated. The implant probe 150 may be coupled to the manipulator 56, or may include a tracker 152 with a plurality of markers 50, or both. The implant probe 150 includes at its end, an attachment feature for securing the talar component 104 to the implant probe 150. The implant probe 150, coupled to the manipulator 56 and tracked by the guidance system 20, can be used to guide the talar component 104 onto the pyramidal frustum 136 according to the surgical plan.

The attachment feature 154 includes a complementary geometry to the upper surface of the talar component 104, including a trough to receive the raised, half-cylindrical ridge extending from the dome of the talar component 104. The attachment feature 154 retains the talar component 104 to the implant probe 150 for movement therewith. The attachment feature 154 may include, for example, a mechanical retention, such as a clip or an active or passive suction element. In another alternative, the implant probe may include a magnetic retention, provided that the talar component 104 is formed from a suitable material susceptible of magnetic retention. Using the implant probe, the robotic system 10, including the guidance station 20, can track the placement of the talar component 104 on the pyramidal frustum 136, displaying the relative positions of the tracked objects on the displays 28, 29. Once the talar component 104 is in the proper position according to the surgical plan, the component 104 can be decoupled from the implant probe 150.

In yet a further alternative, the implant probe 150 may omit the attachment feature 154. After the talar component 104 is placed manually on the pyramidal frustum, the implant probe 150 is brought into contact with it, where the complementary curvatures of the talar component 104 and the implant probe 150 engage to provide a constrained relationship between the two. Comparing the location of the implant probe 150, based on the tracker 152 or through the position information from the manipulator arm, with the tracked talus Ta, the precise placement of the talar component 104 on the pyramidal frustum 136 is determined.

Figure 14:
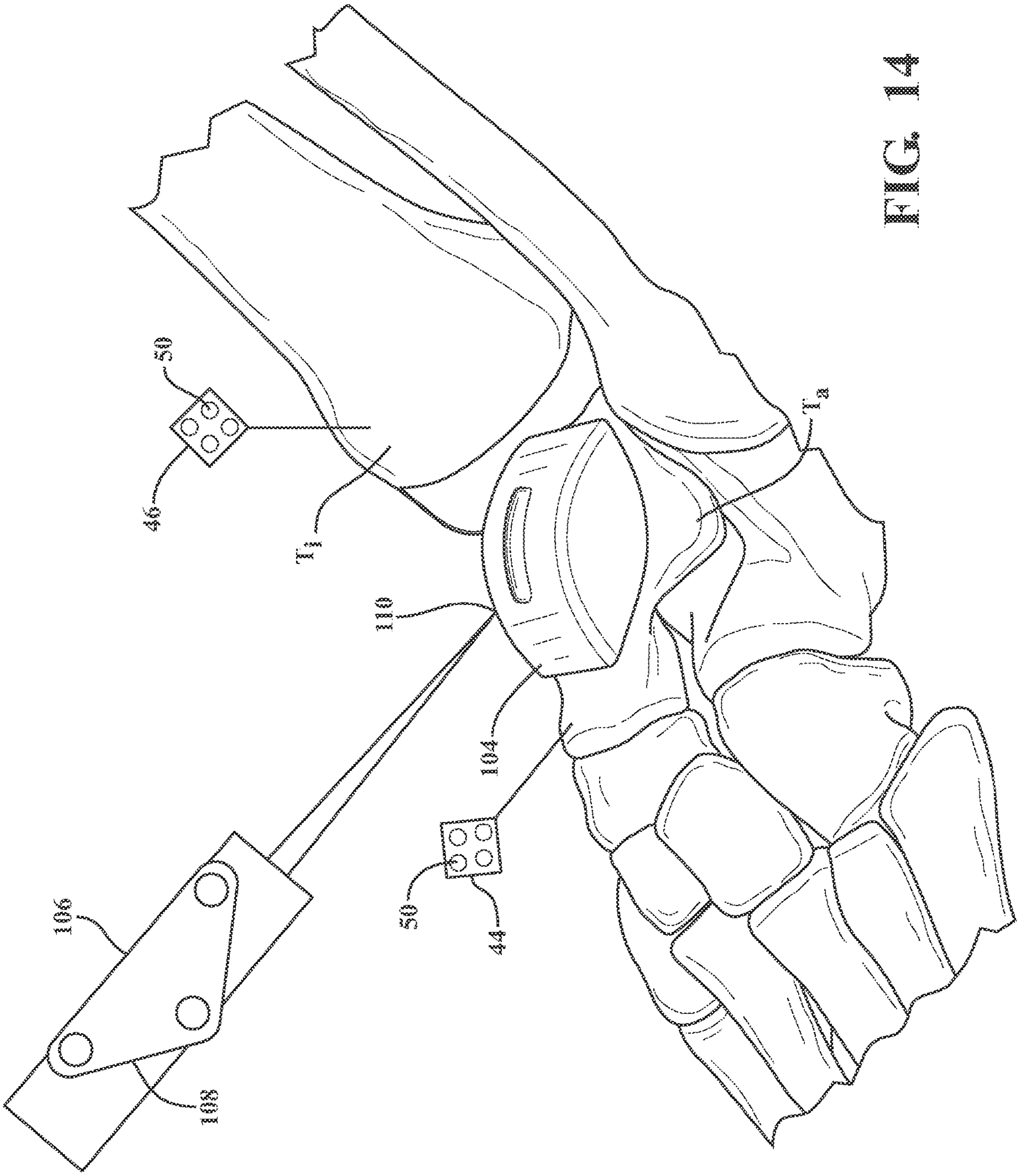
FIG. 14 is an illustration of a navigation pointer being used to locate landmarks on a talar component.

FIG. 14 illustrates yet a further alternative where, prior to the placement of the talar component 104, a pointer 106 is used to collect a plurality of points along each of the facets 119, 128, 130, 132, 134 of the pyramidal frustum 136, regardless of whether the pyramidal frustum 136 is created on the talus Ta manually, using cutting guides, or through the machining station 12 of the robotic system 10. With the collection of points, the guidance station 20 can generate a virtual model of the pyramidal frustum 136 and register the model to the tracker 44. This allows the guidance system to verify the placement against the surgical plan. Subsequently, the user places the talar implant 104 on the resected talus Ta. Again using the pointer 106, the user designates a plurality of points along the top surface of the talar component to generate, with the guidance station 20, registering a virtual model of the talar component 104. Using an atlas model or other model stored in the navigation controller 26, representative of the geometry of the talar component 104, the guidance station 20 can determine the placement of the talar component 104 on the pyramidal frustum 136.

Figure 15:
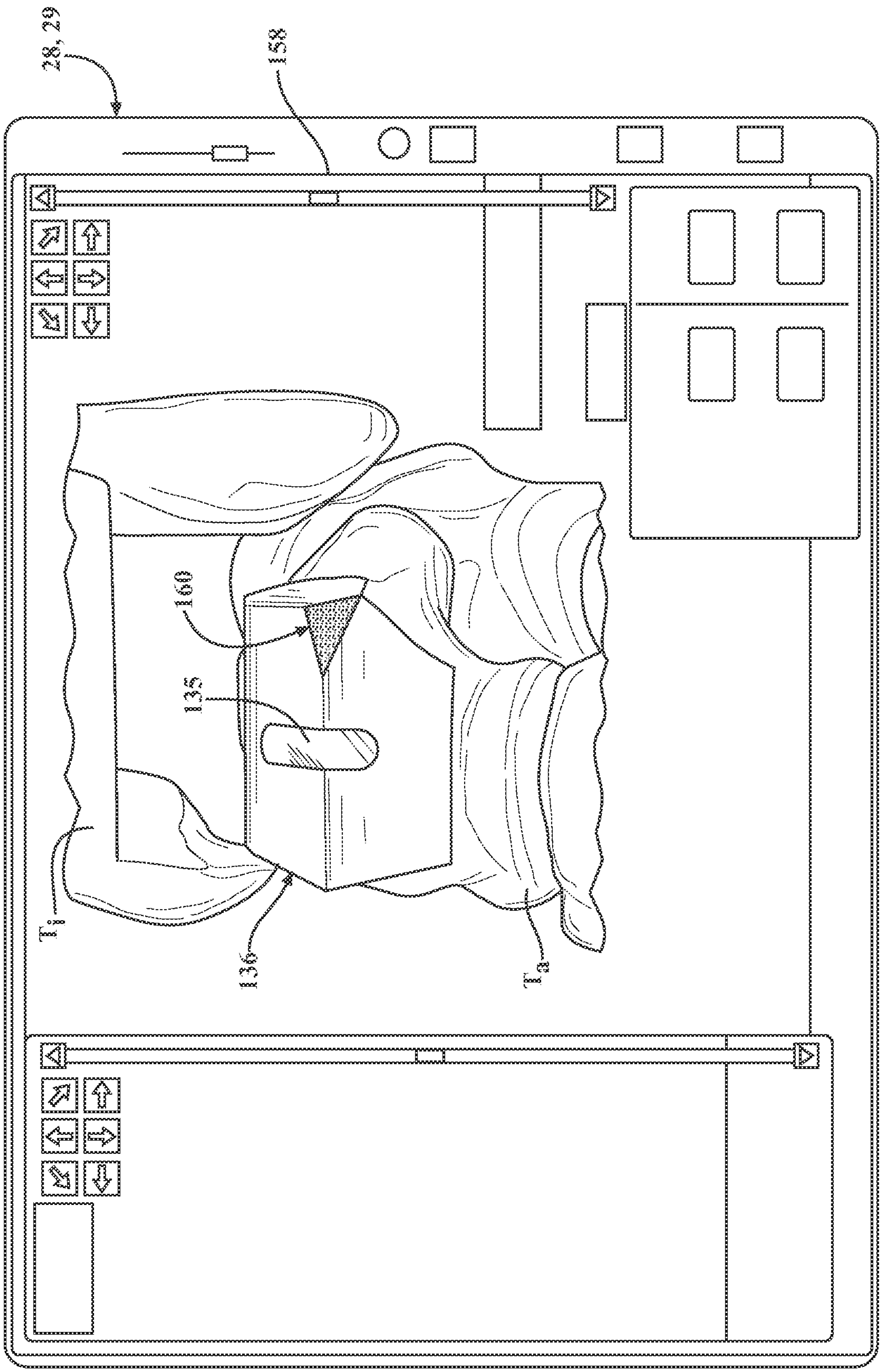
FIG. 15 is an illustration of a graphical user interface providing guidance for correcting the placement of a talar implant.

FIG. 15 illustrates an example graphical user interface 158 such as would be displayed on the first and/or second displays 28, 29, to provide guidance to the user upon a determination that either the pyramidal frustum 136 is improperly shaped on the talus Ta, or that the talar component 104 is not properly seated onto the pyramidal frustum 136. In the example illustrated, an anterior, lateral corner 160 is highlighted to the user to represent either that an insufficient amount of material was removed from this area, or that the talar component 104 is not fully seated in this area. For example, a graphical representation of the pyramidal frustum 136 is generated by the navigation controller 26 on one or both of the displays 28, 29 in one color with the lateral corner 160 highlighted in another color to show the interference between this portion of the pyramidal frustum 136 and the talar component 104 that is preventing the talar component 104 from being properly seated. The graphical representation of the lateral corner 160 may also glow, blink, etc. to further illustrate to the user the location that requires further machining. In another example, not shown, a graphical representation of the patient's talus Ta, along with the planned resection may be shown compared to the actual resection (collected by the navigation pointer 106) to show to the user how close the actual resection is to the planned resection. The guidance station 20 may further provide a recommended corrective action to take, via graphical or text instructions, including generating a virtual/haptic volume of material to be removed in order to correct the determined deviation from the surgical plan. Based on the recommended corrective action, the user may impact the talar component 104 at the location indicated to fully seat it on the talus Ta, or may remove the talar component 104 (if previously placed) in order to access the talus Ta for further machining with the machining station 12 or manual removal of material from the talus Ta. Thereafter, the placement of the talar component 104 on the talus Ta can again be checked for proper seating, etc.

Once the talus Ta has been prepared to receive the talar component 104, the tibia Ti must also be prepared to receive the parallel cylindrical barrels of the tibial component 102. Linear haptic objects 161, 163 may be generated/placed to guide a drill, burr, or mill in forming the barrel holes in the anterior surface of the tibia Ti adjacent to the transverse distal tibial cut described above. Consistent with the above description, the robotic system 10 can be used to maintain the drill on-axis with the linear haptic objects 161, 163 defining the barrel holes. In an alternative, a barrel hole guide (not shown) may be employed to guide the manual drilling of the barrel holes.

Figure 16:
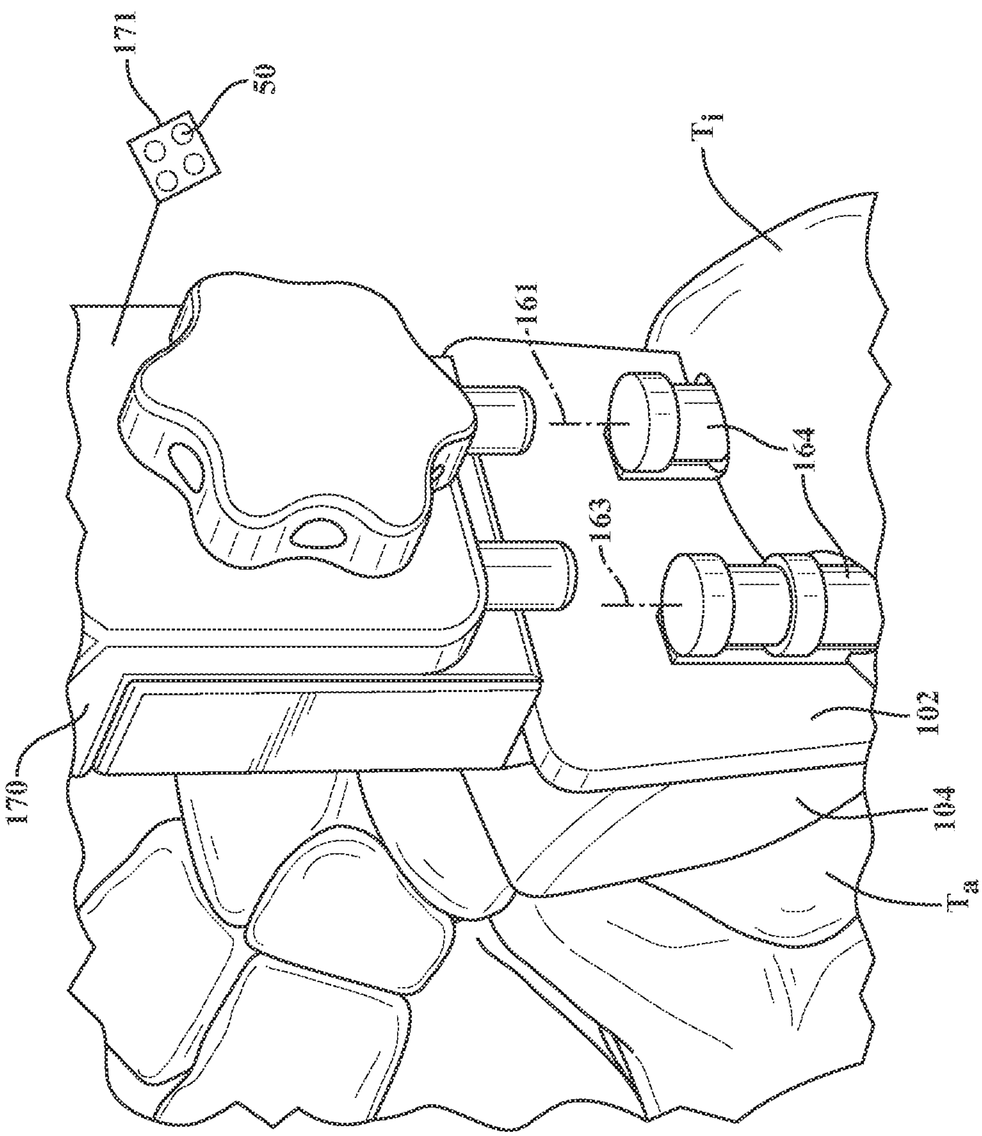
FIG. 16 is an illustration of a tool of the robotic system for installing the tibial component.

FIG. 16 illustrates the installation of the tibial component 102 to the prepared tibia Ti, showing the linear haptic objects 161, 163. A tibial inserter 170 interfaces with the tibial component 102 to aid in the insertion. The tibial inserter 170 may be removably coupled to the manipulator 56, or may include a tracker 171 with a plurality of markers 50 visible to the guidance station 20, or both. The tibial inserter 170 may be configured to mechanically clamp onto the tibial component 102. The tibial inserter 170, including a tracker or coupled to the manipulator 56, can be tracked to aid in the installation of the tibial component 102, and the relative position of the tracked objects can be displayed to the user on the first and/or second displays 28, 29. The barrels of the tibial component 102 will fully seat recessed into the barrel holes, and bone graft material may be packed in to fill the holes.

Figure 17:
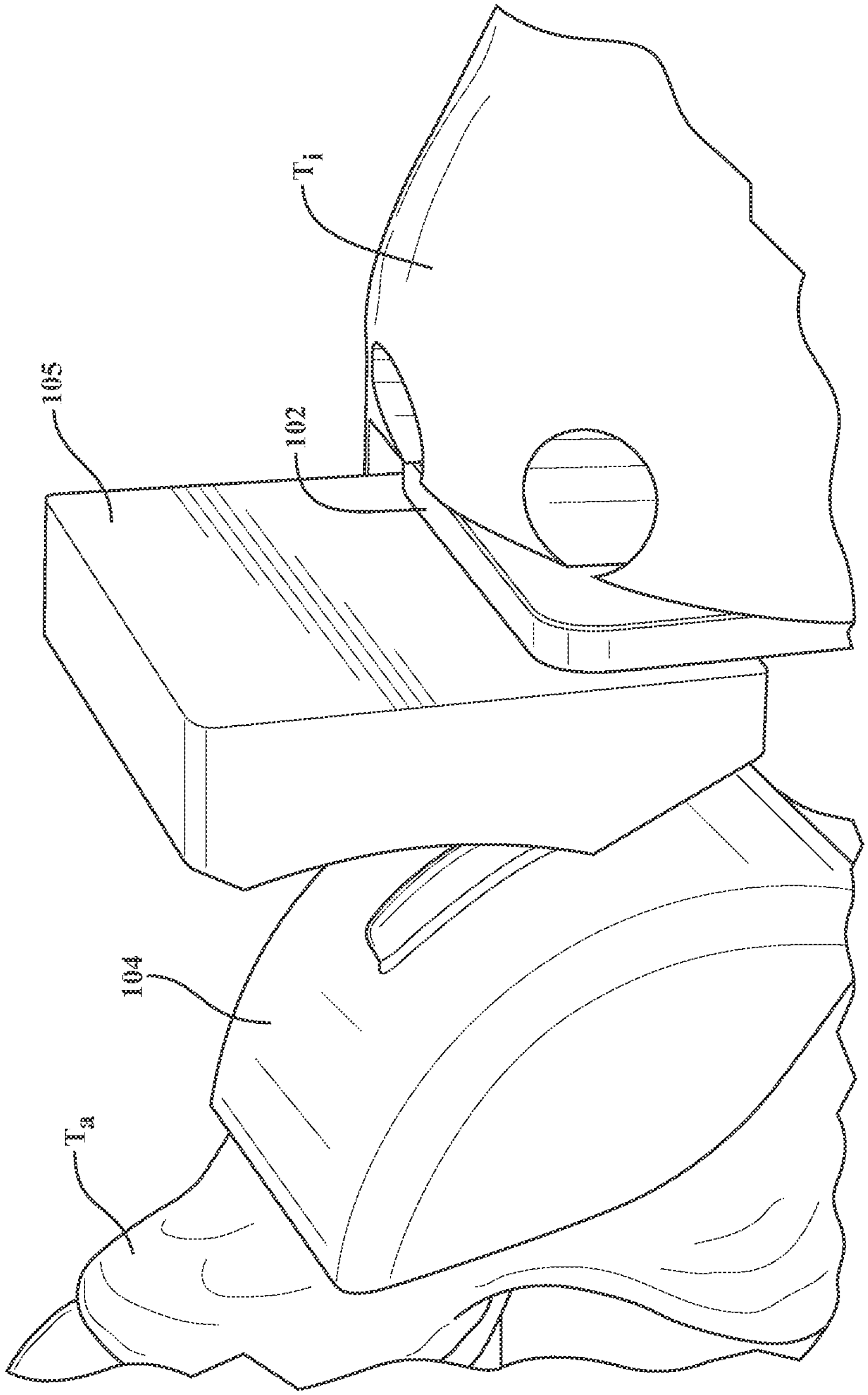
FIG. 17 is an illustration of the insert being installed in the ankle joint.

Once the tibial component 102 and the talar component 104 have been installed to the prepared tibia Ti and talus Ta, the insert 105 can be inserted between the two components 102, 103 to complete the ankle implant system 100, as shown in FIG. 17.

Figure 18:
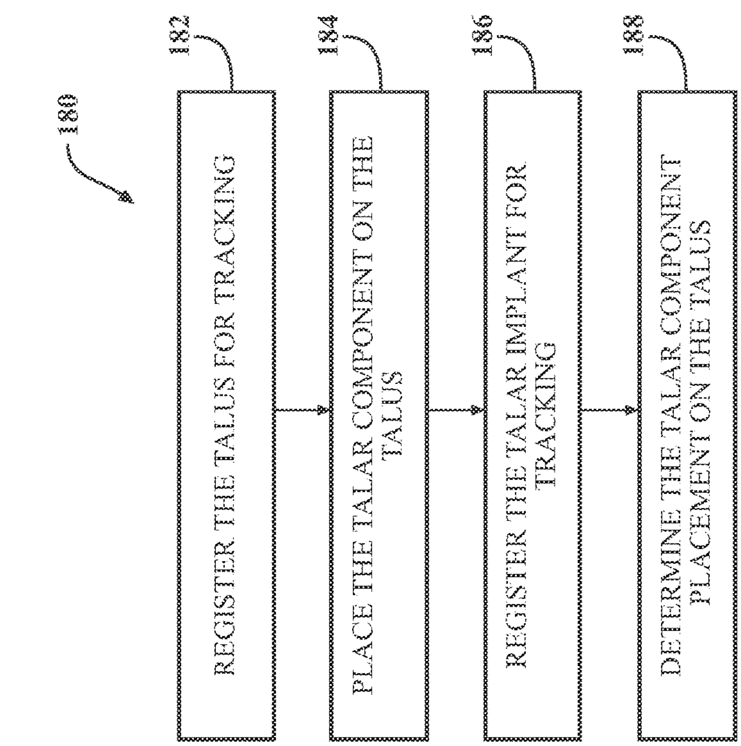
FIG. 18 is a flowchart detailing the procedure for verifying a placement of a talar component.

Consistent with the above description, a method 180 for verifying the placement of a talar component 104 of an ankle implant system 100 on a talus Ta includes the following actions, as illustrated in FIG. 18. The first action 182 includes registering the talus Ta for tracking with a computer surgical system 10. The talar component 104 has a known geometry stored in the memory of the computer surgical system 10. The computer surgical system 10 may be a robotic surgical system 10, including machining station 12 and a guidance station 20. In one alternative, the computer surgical system 10 includes only a guidance station 20. The talus Ta may include a tracker 44 having markers 50 detectable by a guidance station 20 of the computer surgical system 10. In a further alternative, the talus Ta may be tracked by an optical vision system. In some alternatives, registering the talus Ta for tracking includes using a pointer 106 to generate a point cloud corresponding to physical landmarks on the talus Ta and associating the point cloud with corresponding landmarks on a virtual model of the talus Ta. In some alternatives, registering the talus Ta is performed by playing a probe 140 in contact with the talus Ta, while the probe is coupled to a robotic surgical system's manipulator 56. The method may optionally include, prior to registering the talus Ta, preoperatively imaging the talus Ta, generating a virtual model of the talus Ta based on the preoperative imaging and/or placing a tracker on the talus Ta.

The method 180 further includes the action 184 placing the talar implant 104 on the talus Ta. In certain alternatives, prior to placing the talar implant 104 on the talus Ta, the talus Ta is resected in order to receive the talar implant 104. In a further example, the talus Ta is resected by a machining station 12 of the computer surgical system 10. In yet a further example, the talus 104 is resected to form a pyramidal frustum 136 on a proximal aspect of the talus Ta.

The method further includes the action 186 registering the talar implant 104 for tracking with computer surgical system 10. The talar implant 104 may include, or may be coupled, directly or indirectly, to a tracker having markers 50 detectable by the guidance station 20 of the computer surgical system 10. In certain alternatives, the talar implant 104 is coupled to an implant probe 105. The implant probe 150 may, in some alternatives, be coupled to a manipulator 56 of the computer surgical system's 10 machining station 12. In such case, the action 186 of registering the talar implant 104 for tracking includes coupling the talar implant 104 to the implant probe 150 and registering a tracker 152 of the implant probe 150 to the talar implant 104. In some alternatives, the action 186 of registering the talar implant 104 includes placing a probe 150 in contact with the talar implant 104, where the probe 150 includes a complementary curvature to the talar implant 104 sufficient to define a position and orientation of the talar implant 104 when the probe 150 is abutted to the proximal implant surface and the complementary curvatures are aligned. In other alternatives, the action 186 of registering the talar implant 104 for tracking includes using a pointer 106 to generate a point cloud representing physical landmarks of the talar implant 104 and associating the point cloud with corresponding landmarks on a virtual model of the talar implant 104 within a virtually represented navigated space of the guidance station 20.

The method further includes the action 188 determining the talar implant placement on the talus Ta. The action 188 of determining the talar implant placement on the talus Ta may include relating the registered geometry and location of the talar implant 104 to the registered geometry and location of the talus Ta, and evaluating whether an offset or a misalignment exists between the talar implant 104 and the talus Ta relative to a surgical plan for fully seating and aligning the talar implant 104 to the talus Ta.

The method may further include the optional step of providing guidance to the user when there is a determination that the talar implant 104 is misplaced on the talus Ta. The step of providing guidance may include visualizing the placement of the talar implant 104 relative to the talus Ta on a display 28, 29 of the computer surgical system 10 to illustrate the misplacement of the talar implant 104 on the talus Ta. The step of providing guidance may also, or instead, include designating a location of the talar implant 104 to impact in order to correct the misplacement of the talar implant 104 on the talus Ta. The action 188 of providing guidance may also, or instead, include designating a volume of material to be removed from the talus 104 to correct the misplacement of the talar implant 104 on the talus Ta. The step of providing guidance may also, or instead, include indicating a different size talar implant 104 to employ to correct the misplacement. In some alternatives, the action 188 of displaying the misplacement of the talar implant 104 on the talus Ta may include visualizing the actual location of the talar implant 104 on the talus Ta and visualizing a desired location of the talar implant 104 on the talus. In some alternatives, displaying the misplacement of the talar implant 104 on the talus Ta may include highlighting a region of misalignment between the actual location and the desired location of the talar implant 104.

Figure 19:
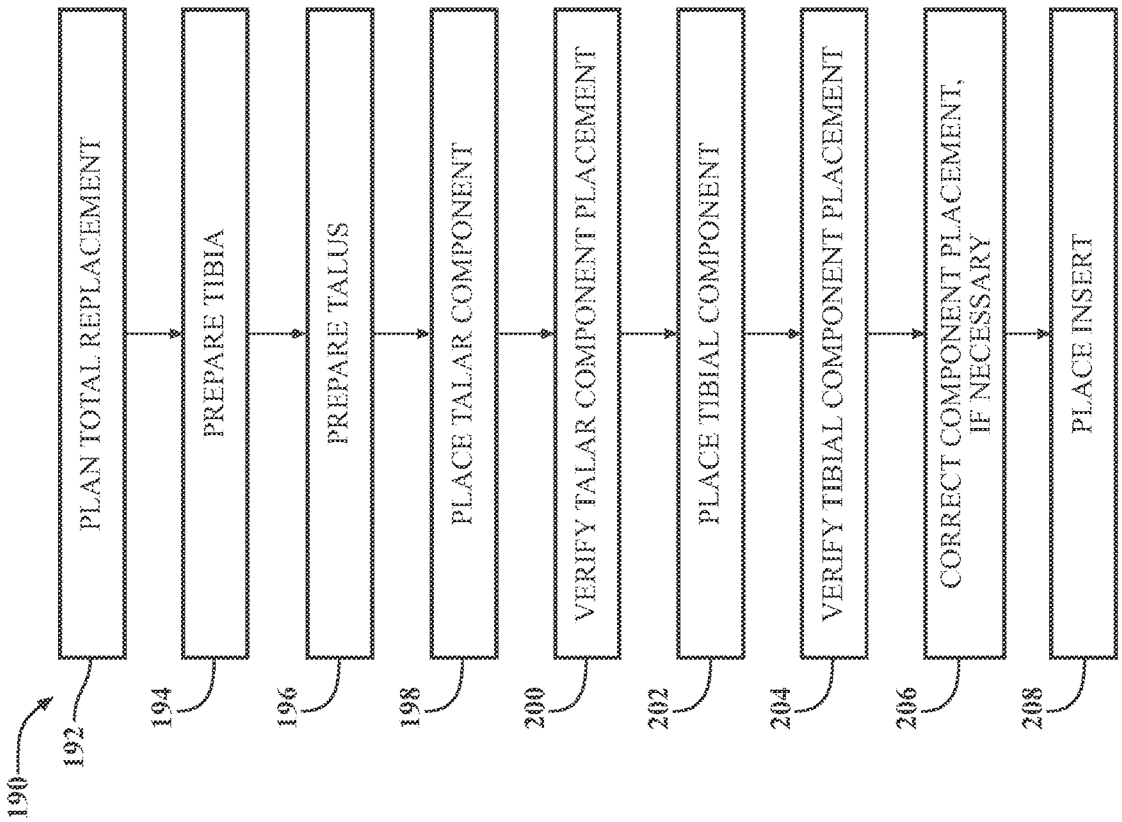
FIG. 19 is a flowchart detailing the procedure for installing an ankle implant.

In an alternative, a method 190 for installing a total ankle replacement 100, including a tibial component 102, a talar component 104, and a mobile bearing 105, includes the following actions, as illustrated in FIG. 19. The first action 192 of the method 190 includes planning the operation, which may further include planning the location of the total ankle replacement 100 in the patient's anatomy and the location of the material to be removed from the tibia Ti and talus Ta to accommodate the total ankle replacement 100, and the resection planes, lines or volumes to accomplish the material removal. Where the operation includes the use of computer surgical system 10, having a machining station 12 and a guidance station 20, planning the resection planes, lines or volumes representing material removal, may further include generating virtual/haptic objects to represent those planes, lines and volumes and tool paths for the movement of a manipulator 56 to traverse an energy applicator EA to perform the required material removal.

The method 190 further includes the action 194 of preparing the tibia Ti to receive a tibial component 102 of the total ankle replacement 100. Preparing the tibia Ti may include resecting the tibia Ti along the medial malleolus, and along a transverse distal aspect substantially perpendicular to the diaphysis of the tibia Ti. Preparing the tibia Ti may further include forming parallel, cylindrical barrel holes adjacent to the transverse distal resection.

The method further includes the action 196 preparing the talus Ta to receive a talar component 104 of the total ankle replacement 100. The action 196 of preparing the talus Ta may include resecting the talus Ta to form a pyramidal frustum 136 having proximal, anterior, posterior, lateral and medial facets 119, 128, 130, 132, 134. Preparing the talus may include forming a keel pocket 135 to receive a keel 107 of the talar component 104.

The method further includes the action 198 of installing the talar component 104 to the prepared talus Ta, and the action 200 of verifying the talar component 104 placement on the talus Ta relative to the surgical plan developed at action 192. The process for installing and verifying the talar component 104 on the talus Ta is performed as has been described above, and in particular in the method 180.

The method 190 further includes the action 202 installing the tibial component 102 to the prepared tibia Ti. The method 190 includes the action 204 verifying the placement of the tibial component 102 to the tibia Ti relative to the surgical plan developed at action 192. The process for installing and verifying the tibial component 102 on the tibia Ti is performed as has been described above. Particularly, the process for installing and verifying the tibial component 102 on the tibia Ti may be performed by following the same sequence of steps and action described in method 180 with regard to the talar component 104 on the talus Ta.

The method 190 may optionally include an action 206 of correcting the placement of the tibial component 102 and/or the talar component 104 if it is determined that the placement of the tibial component 102 or talar component 104 deviates from the surgical plan developed at step 192. The determination that the placement of one or the other of the components deviates from the surgical plan may be indicated to the user in a number of ways that have been described above in multiple alternatives. Additionally, the corrective action or actions taken by the user to rectify the placement of the deviating component have also been described above in multiple alternatives. Finally, the method 190 includes the action 208 of placing the mobile bearing insert 105 between the tibial component 102 and the talar component 104 to complete the total ankle replacement 100.

Several alternatives have been discussed in the foregoing description. However, the discussion herein is not intended to be exhaustive or limiting to any particular form. The terminology which has been used is intended to be in the nature of words of description rather than of limitation. Many modifications and variations are possible in light of the above teachings and may be practiced otherwise than as specifically described.

What is claimed is:

1. A method for performing surgery on a talus, the method comprising:

providing a localizer for tracking one or more objects in a coordinate system;

registering the talus for tracking in the coordinate system with a computer surgical system using the localizer;

providing a cutting tool;

tracking movement of the cutting tool and the talus with the computer surgical system using the localizer;

resecting the talus with the cutting tool;

placing a talar implant on the talus, the talar implant having a known geometry;

registering the talar implant for tracking in the coordinate system with the computer surgical system using the localizer; and determining a placement of the talar implant on the talus with the computer surgical system by comparing locations in the coordinate system of the registered talus and the registered talar implant determined with the localizer relative to a predetermined surgical plan for seating the talar implant to the talus.

2. The method of claim 1, wherein resecting the talus with the cutting tool includes controlling the cutting tool to form a pyramidal frustum on the talus adapted to receive the talar implant.

3. The method of claim 1, wherein resecting the talus with the cutting tool includes controlling the cutting tool based on locations in the coordinate system of the registered talus and the cutting tool.

4. The method of claim 1, wherein resecting the talus with the cutting tool includes controlling movement of the cutting tool relative to the talus using a robotic manipulator supporting the cutting tool based on one or more virtual objects associated with the talar implant.

5. The method of claim 4, wherein the one or more virtual objects comprise a virtual cutting boundary.

6. The method of claim 5, comprising generating haptic feedback to a user based on a position of the cutting tool relative to the virtual cutting boundary.

7. The method of claim 5, comprising controlling movement of the cutting tool in a haptic mode of the robotic manipulator in which a user manually manipulates the cutting tool to resect the talus and the robotic manipulator generates haptic feedback in response to the cutting tool reaching or exceeding the virtual cutting boundary.

8. The method of claim 5, comprising controlling movement of the cutting tool in a free mode of the robotic manipulator in which a user is allowed to freely manipulate the cutting tool beyond the virtual cutting boundary.

9. The method of claim 5, comprising controlling movement of the cutting tool in an autonomous mode of the robotic manipulator to control movement of the cutting tool autonomously along a tool path to resect the talus.

10. The method of claim 5, comprising:

determining positions of a plurality of landmarks on the talus;

defining a virtual material removal volume in the coordinate system based on the positions of the plurality of landmarks, the coordinate system being registered to the talus; and defining the one or more virtual objects in the coordinate system based on a location of the virtual material removal volume.

11. The method of claim 1, further comprising the step of providing guidance on a display when the step of determining the talar implant placement determines that the talar implant is misplaced on the talus, wherein the step of providing guidance includes visualizing the placement of the talar implant on the talus to display a misplacement of the talar implant on the talus; and wherein visualizing the placement of the talar implant on the talus displays an actual location of the talar implant and displays a desired location of the talar implant, and further comprises highlighting a region of misalignment between the actual location of the talar implant and the desired location of the talar implant.

12. The method of claim 1, further comprising, prior to registering the talus, preoperatively imaging the talus; generating a virtual model of the talus based on the preoperative imaging; and placing a tracker on the talus.

13. The method of claim 1, wherein registering the talus is performed by one or more of:

placing a pointer in contact with the talus, the pointer having a tracker;

placing a probe in contact with the talus, the probe coupled to a robotic manipulator, wherein the robotic manipulator includes one or more joint encoders; and intraoperatively imaging the talus.

14. The method of claim 1, further comprising the step of providing guidance on a display when the step of determining the talar implant placement determines that the talar implant is misplaced on the talus, wherein the step of providing guidance includes visualizing, on the display, a location on the talar implant to impact in order to correct the misplacement of the talar implant on the talus.

15. The method of claim 1, further comprising the step of providing guidance on a display when the step of determining the talar implant placement determines that the talar implant is misplaced on the talus, wherein the step of providing guidance includes visualizing, on the display, a volume of material to be removed from the talus to correct the misplacement of the talar implant on the talus.

16. The method of claim 1, further comprising the step of providing guidance on a display when the step of determining the talar implant placement determines that the talar implant is misplaced on the talus, wherein the step of providing guidance includes indicating a different sized talar implant to correct the misplacement.

17. The method of claim 1, wherein registering the talus includes registering a plurality of talus points on a resected surface of the talus using a pointer having a tracker, the localizer being configured to track the tracker of the pointer in the coordinate system.

18. The method of claim 1, further comprising, prior to registering the talus, placing a tracker on the talus, the localizer being configured to track the tracker of the talus in the coordinate system.

19. The method of claim 1, wherein registering the talus includes placing a pointer having a tracker in contact with the talus, the localizer being configured to track the tracker of the pointer in the coordinate system.

20. The method of claim 1, wherein registering the talar implant includes placing a pointer having a tracker in contact with the talar implant, the localizer being configured to track the tracker of the pointer in the coordinate system.

* * * * *